(12) United States Patent
Schenk

(10) Patent No.: US 7,618,770 B2
(45) Date of Patent: Nov. 17, 2009

(54) METHODS AND APPARATUS FOR REDUCING PROTEIN CONTENT IN SPERM CELL EXTENDERS

(75) Inventor: John L. Schenk, Fort Collins, CO (US)

(73) Assignee: XY, Inc., Fort Collins, CO (US)

( * ) Notice: Subject to any disclaimer, the term of this patent is extended or adjusted under 35 U.S.C. 154(b) by 4 days.

(21) Appl. No.: 11/219,607

(22) Filed: Sep. 2, 2005

(65) Prior Publication Data

US 2007/0026378 A1 Feb. 1, 2007

Related U.S. Application Data

(60) Provisional application No. 60/704,001, filed on Jul. 29, 2005.

(51) Int. Cl.
*A01N 1/02* (2006.01)
(52) U.S. Cl. .......................... 435/2; 435/325; 424/93.7
(58) Field of Classification Search ...................... 435/2, 435/325; 424/93.7
See application file for complete search history.

(56) References Cited

U.S. PATENT DOCUMENTS

| | | | |
|---|---|---|---|
| 3,299,354 A | 1/1967 | Hogg |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,756,459 A | 9/1973 | Bannister |
| 3,761,941 A | 9/1973 | Robertson |
| 3,810,010 A | 5/1974 | Thom |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,909,744 A | 9/1975 | Wisner et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| RE29,141 E | 2/1977 | Hogg |
| 4,007,087 A | 2/1977 | Ericsson |
| 4,009,260 A | 2/1977 | Ericsson |
| 4,014,611 A | 3/1977 | Simpson et al. |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |
| 4,092,229 A | 5/1978 | Bhattacharya |
| 4,155,831 A | 5/1979 | Bhattacharya |
| 4,162,282 A | 7/1979 | Fulwyler et al. |
| 4,178,936 A | 12/1979 | Newcomb |
| 4,179,218 A | 12/1979 | Erdmann et al. |
| 4,191,749 A | 3/1980 | Bryant |
| 4,200,802 A | 4/1980 | Salzman et al. |
| 4,225,405 A | 9/1980 | Lawson |
| 4,230,558 A | 10/1980 | Fulwyler |
| 4,255,021 A | 3/1981 | Brunsden |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,350,410 A | 9/1982 | Minott |

(Continued)

FOREIGN PATENT DOCUMENTS

BR 9704313 6/1999

(Continued)

OTHER PUBLICATIONS

"Applying Semen Sexing Technology to the AI Industry", National Association of Animal Breeders, Sep. 2000, pp. 1-16.

(Continued)

*Primary Examiner*—Ruth A Davis
(74) *Attorney, Agent, or Firm*—Santangelo Law Offices, P.C.

(57) ABSTRACT

The inventive technology relates to methods and apparatus for reducing protein content in sperm cell extenders and may include one or more of the following features: techniques for reducing protein content in a sperm cell extender; techniques for reducing protein content in a cryoprotectant-containing B fraction of a sperm cell extender; techniques for preparing sperm cell extenders that do not require clarification; techniques for preparing low density gradient sperm cell extenders suitable for centrifugation; techniques for reducing protein content between individual steps in preparing a sperm cell extender, and techniques for establishing novel values of reduced protein content in sperm cell extenders.

50 Claims, 5 Drawing Sheets

U.S. PATENT DOCUMENTS

| | | |
|---|---|---|
| 4,352,558 A | 10/1982 | Eisert |
| 4,361,400 A | 11/1982 | Gray et al. |
| 4,362,246 A | 12/1982 | Adair |
| 4,395,397 A | 7/1983 | Shapiro |
| 4,395,676 A | 7/1983 | Hollinger et al. |
| 4,400,764 A | 8/1983 | Kenyon |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,559,309 A | 12/1985 | Evenson |
| 4,573,796 A | 3/1986 | Martin |
| 4,598,408 A | 7/1986 | O'Keefe |
| 4,600,302 A | 7/1986 | Sage, Jr. |
| 4,605,558 A | 8/1986 | Shrimpton |
| 4,631,483 A | 12/1986 | Proni et al. |
| 4,637,691 A | 1/1987 | Uehara et al. |
| RE32,350 E | 2/1987 | Bhattacharya |
| 4,654,025 A | 3/1987 | Cassou et al. |
| 4,660,971 A | 4/1987 | Sage et al. |
| 4,673,288 A | 6/1987 | Thomas et al. |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,714,680 A | 12/1987 | Civin |
| 4,744,090 A | 5/1988 | Freiberg |
| 4,749,458 A | 6/1988 | Muroi et al. |
| 4,756,427 A | 7/1988 | Gohde et al. |
| 4,758,729 A | 7/1988 | Monnin |
| 4,764,013 A | 8/1988 | Johnston |
| 4,780,451 A | 10/1988 | Donaldson |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,877,965 A | 10/1989 | Dandliker et al. |
| 4,942,305 A | 7/1990 | Sommer |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junilla |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | De Grooth |
| 5,021,244 A | 6/1991 | Spaulding |
| 5,030,002 A | 7/1991 | North, Jr. |
| 5,034,613 A | 7/1991 | Denk et al. |
| 5,055,393 A | 10/1991 | Kwoh et al. |
| 5,079,959 A | 1/1992 | Miyake et al. |
| 5,084,004 A | 1/1992 | Ranoux |
| 5,088,816 A | 2/1992 | Tomioka et al. |
| 5,098,657 A | 3/1992 | Blackford et al. |
| 5,101,978 A | 4/1992 | Marcus |
| 5,127,729 A | 7/1992 | Oetliker et al. |
| 5,132,548 A | 7/1992 | Borden et al. |
| 5,135,759 A | 8/1992 | Johnson |
| 5,144,224 A | 9/1992 | Larsen |
| 5,150,313 A | 9/1992 | Van den Engh et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,298,967 A | 3/1994 | Wells |
| 5,315,122 A | 5/1994 | Pinsky et al. |
| 5,346,990 A | 9/1994 | Spaulding |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. |
| 5,412,466 A | 5/1995 | Ogino |
| 5,437,987 A | 8/1995 | Ten et al. |
| 5,439,362 A | 8/1995 | Spaulding |
| 5,447,842 A | 9/1995 | Simons |
| 5,452,054 A | 9/1995 | Dewa et al. |
| 5,461,145 A | 10/1995 | Kudo et al. |
| 5,466,572 A | 11/1995 | Sasaki et al. |
| 5,467,189 A | 11/1995 | Kreikebaum et al. |
| 5,471,294 A | 11/1995 | Ogino |
| 5,471,299 A | 11/1995 | Kaye et al. |
| 5,480,774 A | 1/1996 | Hew et al. |
| 5,483,469 A | 1/1996 | Van den Engh et al. |
| 5,492,534 A | 2/1996 | Atheyde |
| 5,494,795 A | 2/1996 | Guerry et al. |
| 5,496,272 A | 3/1996 | Chung et al. |
| 5,503,994 A | 4/1996 | Shear et al. |
| 5,514,537 A | 5/1996 | Chandler |
| 5,523,573 A | 6/1996 | Hanninen et al. |
| 5,532,155 A | 7/1996 | Ranoux |
| 5,558,998 A | 9/1996 | Hammond et al. |
| 5,559,032 A | 9/1996 | Pomeroy et al. |
| 5,578,449 A | 11/1996 | Frasch et al. |
| 5,589,457 A | 12/1996 | Wiltbank |
| 5,596,401 A | 1/1997 | Kusuzawa |
| 5,601,235 A | 2/1997 | Booker et al. |
| 5,601,533 A | 2/1997 | Hancke et al. |
| 5,602,039 A | 2/1997 | Van den Engh |
| 5,602,349 A | 2/1997 | Van den Engh |
| 5,622,820 A | 4/1997 | Rossi |
| 5,641,457 A | 6/1997 | Vardanega |
| 5,643,796 A | 7/1997 | Van Den Engh et al. |
| 5,650,847 A | 7/1997 | Maltsev et al. |
| 5,660,997 A | 8/1997 | Spaulding |
| 5,663,048 A | 9/1997 | Winkfein et al. |
| 5,665,315 A | 9/1997 | Robert et al. |
| 5,672,880 A | 9/1997 | Kain |
| 5,675,401 A | 10/1997 | Wangler et al. |
| 5,684,575 A | 11/1997 | Steen |
| 5,687,727 A | 11/1997 | Kraus et al. |
| 5,690,815 A | 11/1997 | Krasnoff et al. |
| 5,690,895 A | 11/1997 | Matsumoto et al. |
| 5,691,133 A | 11/1997 | Critser et al. |
| 5,693,534 A | 12/1997 | Alak et al. |
| 5,700,692 A | 12/1997 | Sweet |
| 5,707,808 A | 1/1998 | Roslaniec et al. |
| 5,708,868 A | 1/1998 | Ishikawa |
| 5,726,364 A | 3/1998 | Van den Engh |

| | | | | | | |
|---|---|---|---|---|---|---|
| 5,759,767 | A | 6/1998 | Lakowicz et al. | 6,761,286 B2 | 7/2004 | Py et al. |
| 5,777,732 | A | 7/1998 | Hanninen et al. | 6,761,288 B2 | 7/2004 | Garcia |
| 5,780,230 | A | 7/1998 | Li et al. | 6,782,768 B2 | 8/2004 | Buchanan et al. |
| 5,786,560 | A | 7/1998 | Tatah et al. | 6,789,706 B2 | 9/2004 | Abergel et al. |
| 5,793,485 | A | 8/1998 | Gourley | 6,789,921 B1 | 9/2004 | Heldt |
| 5,796,112 | A | 8/1998 | Ichie | 6,793,387 B1 | 9/2004 | Neas et al. |
| 5,799,830 | A | 9/1998 | Carroll et al. | 6,819,411 B1 | 11/2004 | Sharpe et al. |
| 5,804,436 | A | 9/1998 | Okun et al. | 7,094,527 B2 | 8/2006 | Seidel et al. |
| 5,815,262 | A | 9/1998 | Schrof et al. | 7,105,355 B2 | 9/2006 | Kurabayashi et al. |
| 5,819,948 | A | 10/1998 | Van den Engh | 7,195,920 B2 | 3/2007 | Seidel et al. |
| 5,824,269 | A | 10/1998 | Kosaka et al. | 7,208,265 B1 * | 4/2007 | Schenk .................. 435/1.1 |
| 5,835,262 | A | 11/1998 | Iketaki et al. | 7,221,453 B2 | 5/2007 | Sharpe et al. |
| 5,868,767 | A | 2/1999 | Farley et al. | 2002/0096123 A1 | 7/2002 | Whittier et al. |
| 5,873,254 | A | 2/1999 | Arav | 2002/0113965 A1 | 8/2002 | Roche et al. |
| 5,876,942 | A | 3/1999 | Cheng et al. | 2002/0119558 A1 | 8/2002 | Seidel et al. |
| 5,880,457 | A | 3/1999 | Tomiyama et al. | 2002/0141902 A1 | 10/2002 | Ozasa et al. |
| 5,888,730 | A | 3/1999 | Gray et al. | 2002/0186375 A1 | 12/2002 | Asbury et al. |
| 5,891,734 | A | 4/1999 | Gill et al. | 2003/0002027 A1 | 1/2003 | Fritz |
| 5,893,843 | A | 4/1999 | Claro | 2003/0098421 A1 | 5/2003 | Ho |
| 5,895,764 | A | 4/1999 | Sklar et al. | 2003/0129091 A1 | 7/2003 | Seidel et al. |
| 5,895,922 | A | 4/1999 | Ho | 2003/0157475 A1 * | 8/2003 | Schenk ...................... 435/2 |
| 6,704,313 | B1 | 4/1999 | De Resende et al. | 2003/0207461 A1 | 11/2003 | Bell et al. |
| 5,899,848 | A | 5/1999 | Haubrich | 2003/0209059 A1 | 11/2003 | Kawano |
| 5,912,257 | A | 6/1999 | Prasad et al. | 2004/0005582 A1 | 1/2004 | Shipwast |
| 5,916,144 | A | 6/1999 | Prather et al. | 2004/0031071 A1 | 2/2004 | Morris et al. |
| 5,916,449 | A | 6/1999 | Ellwart et al. | 2004/0049801 A1 | 3/2004 | Seidel |
| 5,919,360 | A | 7/1999 | Contaxis, III et al. | 2004/0053243 A1 | 3/2004 | Evans |
| 5,919,621 | A | 7/1999 | Brown | 2004/0055030 A1 | 3/2004 | Maxwell et al. |
| 5,934,885 | A | 8/1999 | Farrell et al. | 2004/0062685 A1 | 4/2004 | Norton et al. |
| 5,985,216 | A | 11/1999 | Rens et al. | 2004/0107150 A1 | 6/2004 | Neas et al. |
| 5,985,538 | A | 11/1999 | Stachecju | 2004/0132001 A1 | 7/2004 | Seidel et al. |
| 6,002,471 | A | 12/1999 | Quake | 2005/0003472 A1 | 1/2005 | Anzar et al. |
| 6,050,935 | A | 4/2000 | Ranoux et al. | 2005/0011582 A1 | 1/2005 | Haug |
| 6,071,689 | A | 6/2000 | Seidel et al. | 2005/0064383 A1 | 3/2005 | Bashkin et al. |
| 6,086,574 | A | 7/2000 | Carroll et al. | 2005/0112541 A1 | 5/2005 | Durack |
| 6,087,352 | A | 7/2000 | Trout | 2005/0214733 A1 | 9/2005 | Graham |
| 6,117,068 | A | 9/2000 | Gourley et al. | 2005/0244805 A1 | 11/2005 | Ludwig et al. |
| 6,119,465 | A | 9/2000 | Mullens et al. | 2005/0282245 A1 | 12/2005 | Ludwig et al. |
| 6,133,044 | A | 10/2000 | Van den Engh | 2006/0118167 A1 | 6/2006 | Neas et al. |
| 6,140,121 | A | 10/2000 | Ellington et al. | 2006/0147894 A1 | 7/2006 | Sowter |
| 6,149,867 | A | 11/2000 | Seidel et al. | 2006/0263829 A1 | 11/2006 | Evans et al. |
| 6,153,373 | A | 11/2000 | Benjamin et al. | 2006/0281176 A1 | 12/2006 | Seidel et al. |
| 6,154,276 | A | 11/2000 | Mariella, Jr. | 2007/0026378 A1 | 2/2007 | Schenk |
| 6,175,409 | B1 | 1/2001 | Nielsen et al. | 2007/0026379 A1 | 2/2007 | Seidel et al. |
| 6,177,277 | B1 | 1/2001 | Soini | 2007/0042342 A1 | 2/2007 | Seidel et al. |
| 6,238,920 | B1 | 5/2001 | Nagai et al. | 2007/0092860 A1 | 4/2007 | Schenk |
| 6,248,590 | B1 | 6/2001 | Malachowski | 2007/0099171 A1 | 5/2007 | Schenk |
| 6,263,745 | B1 | 7/2001 | Buchanan et al. | 2007/0099260 A1 | 5/2007 | Seidel et al. |
| 6,283,920 | B1 | 9/2001 | Eberle et al. | | | |
| 6,328,071 | B1 | 12/2001 | Austin | FOREIGN PATENT DOCUMENTS | | |
| 6,357,307 | B2 | 3/2002 | Buchanan et al. | CN | 03109426.0 | 12/2005 |
| 6,372,422 | B1 | 4/2002 | Seidel et al. | CN | 100998524 | 7/2007 |
| 6,395,305 | B1 | 5/2002 | Buhr et al. | EP | 0025296 A2 | 3/1981 |
| 6,411,835 | B1 | 6/2002 | Modell et al. | EP | 0071538 A1 | 2/1983 |
| 6,463,314 | B1 | 10/2002 | Haruna | EP | 0140616 | 5/1985 |
| 6,489,092 | B1 | 12/2002 | Benjamin et al. | EP | 0160201 A2 | 11/1985 |
| 6,495,366 | B1 | 12/2002 | Briggs | EP | 0189702 A1 | 8/1986 |
| 6,524,860 | B1 | 2/2003 | Seidel et al. | EP | 0288029 B1 | 4/1988 |
| 6,528,802 | B1 | 3/2003 | Koenig et al. | EP | 0276166 A2 | 7/1988 |
| 6,534,308 | B1 | 3/2003 | Palsson et al. | EP | A-0 366794 | 5/1990 |
| 6,537,829 | B1 | 3/2003 | Zarling et al. | EP | 0461618 | 12/1991 |
| 6,577,387 | B2 | 6/2003 | Ross, III et al. | EP | 0468100 A1 | 1/1992 |
| 6,590,911 | B1 | 7/2003 | Spinelli et al. | EP | 0570102 A1 | 3/1993 |
| 6,604,435 | B2 | 8/2003 | Buchanan et al. | EP | 0538786 A | 4/1993 |
| 6,617,107 | B1 | 9/2003 | Dean | EP | 606847 A2 | 7/1994 |
| 6,618,679 | B2 | 9/2003 | Loehrlein et al. | EP | A-0 478155 | 1/1998 |
| 6,642,018 | B1 | 11/2003 | Koller et al. | EP | 1250897 A1 | 10/2002 |
| 6,667,830 | B1 | 12/2003 | Iketaki et al. | EP | 1403633 A3 | 4/2004 |
| 6,671,044 | B2 | 12/2003 | Ortyn et al. | FR | 2574656 A1 | 6/1986 |
| 6,673,095 | B2 | 1/2004 | Nordquist | FR | A-2 635453 | 2/1990 |
| 6,698,627 | B2 | 3/2004 | Garcia et al. | FR | 2 647 668 A | 12/1990 |
| 6,729,369 | B2 | 5/2004 | Neas et al. | FR | 2699678 A1 | 6/1994 |
| 6,752,298 | B2 | 6/2004 | Garcia et al. | | | |

| | | |
|---|---|---|
| GB | 1471019 | 4/1977 |
| JP | 61139747 A | 6/1986 |
| JP | 61159135 A | 7/1986 |
| JP | 2024535 | 1/1990 |
| JP | 4126064 A | 4/1992 |
| JP | 4126065 A | 4/1992 |
| JP | 4126066 A | 4/1992 |
| JP | 4126079 A | 4/1992 |
| JP | 4126080 A | 4/1992 |
| JP | 4126081 A | 4/1992 |
| SU | 1056008 | 11/1983 |
| SU | 1260778 A1 | 9/1986 |
| WO | WO 88/07198 | 9/1988 |
| WO | WO 90/13315 A1 | 11/1990 |
| WO | WO 91/05236 | 4/1991 |
| WO | WO 93/17322 A1 | 9/1993 |
| WO | WO 96/12171 | 4/1996 |
| WO | WO 96/31764 | 10/1996 |
| WO | WO 98/34094 | 8/1998 |
| WO | WO 98/48259 | 10/1998 |
| WO | WO 99/05504 | 2/1999 |
| WO | WO 99/33956 | 7/1999 |
| WO | WO 99/38883 | 8/1999 |
| WO | WO 99/42810 | 8/1999 |
| WO | WO 99/44037 A1 | 9/1999 |
| WO | WO 00/06193 | 2/2000 |
| WO | WO 0129538 | 4/2001 |
| WO | WO 01/37655 A1 | 5/2001 |
| WO | WO 01/40765 A2 | 6/2001 |
| WO | WO 01/40765 A3 | 6/2001 |
| WO | WO 01/51612 A1 | 7/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/19943 A1 | 3/2002 |
| WO | WO 02/028311 A1 | 4/2002 |
| WO | WO 02/41906 A2 | 5/2002 |
| WO | WO 0241906 A2 | 5/2002 |
| WO | WO 02/043486 A1 | 6/2002 |
| WO | WO 02/43574 A3 | 6/2002 |
| WO | WO 03020877 A2 | 3/2003 |
| WO | WO 2004/009237 A2 | 1/2004 |
| WO | WO2004/009237 A2 | 1/2004 |
| WO | WO 2004/012837 A2 | 2/2004 |
| WO | WO 2004/017041 A2 | 2/2004 |
| WO | WO 2004/017041 A3 | 2/2004 |
| WO | WO 2004/024227 A2 | 3/2004 |
| WO | WO 2004/024227 A3 | 3/2004 |
| WO | WO 2004/059282 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | WO 2004/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | WO 2006012597 A2 | 2/2006 |
| WO | WO 2006060770 A2 | 8/2006 |
| WO | WO 2007/016090 A2 | 2/2007 |

OTHER PUBLICATIONS

Akhtar, S., et al. 1995. Prevalence of Five Stereotypes of Bluetongue Virus in a Rambouillet Sheep Flock in Pakistan, Veterinary Record 136, p. 495.
Amann, R.P. and Seidel, G.E. Jr., 1982. Prospects For Sexing Mammalian Sperm, Animal Reproduction Laboratory College of Veterinary Medicine and Biomedical Sciences, Colorado State University ( ).
Amoah, E.A. and Gelaye, S. 1996. Biotechnological advances in goat reproduction. J. Anim. Sci. 75(2):578-585.
Anderson, V.K., et al., 1973. Intrauterine und tiefzervikale Insemination mit Gefriersperma bein Schat. Zuchthygiene. 8:113-118.
Arriola J., et al., Glycerolation and thawing Effects on Bull Spermatozoa Frozen in Detergent—Treated Egg Yolk and Whole Egg Extenders, 1987 J Dairy Sci 70:1664-1670.
Baker, R.D., et al., H.W. 1968. Effect of volume of semen, number of sperm and drugs on transport of sperm in artificially inseminated gilts. J. Anim. Sci. 27:88-93.
Batellier, F, Vidament M, Duchamp G, Arnaud G, Yvon JM, Fauquant J, Magistrini M., Advances in cooled technologies. Anim Reprod Sci 2001; In press.
Barnes, F.L.. and Eyestone, W.H., "Early Cleavage and the Maternal Zygotic Transition in Bovine Embryos", Theriogenology, vol. 33, No. 1, Jan. 1990, pp. 141-149.
Becker, S.E. and Johnson, A.L. 1992. Effects of gonadotropin releasing hormone infused in a pulsatite or continuous fashion on serum gonadotropin concentrations and ovulation in the mare. J. Anim. Sci. 70:1208-1215.
Bedford, S .J. and Hinrichs, K. 1994. The effect of insemination volume on pregnancy rates of pony mares. Theriogenology 42:571-578.
Berger, G.S. 1987. Intratubal insemination. Fert. Steril. 48:328-330.
Beyhan, Z., et al., 1998. Sexual dimorphism in IVF bovine embryos produced by sperm sorted by high speed flow cytometry. Theriogenology. 49(1):359. abstr.
Beyhan, Z., et al., 1999. Sexual dimorphism in IVM-IVF bovine embryos produced from X and Y Chromosome-Bearing spermatozoa sorted by high speed flow cytometry. Theriogenology. 52:35-48.
Blanchard, T. and Dickson, V., "Stallion Management", The Veterinary Clinics of North America, Equine Practice, vol. 8, No. 1, pp. 207-218 (1992).
Bioxcell, Bovine Sperm Preservation, Advertisement Jun. 28, 2005.
Bracher, V. and Allen, W.R., "Videoendoscopic Examination of the Mare's Uterus: Findings in Normal Fertile Mares", Equine Veterinary Journal, vol. 24 (1992), pp. 274-278.
Braselton, W.E. and McShan, W.H. 1970. Purification and properties of follicle stimulating and luteinizing hormones from horse pituitary glands. Arch. Biochem. Biophys. 139:45-48.
Brethour, J.R. and Jaeger, J.R., "The Single Calf Heifer System", Kansas Agric. Sta. Rep of Progress 570, 1989.
Bristol, S.P. 1982. Breeding behavior of a stallion at pasture with 20 mares in synchronized oestrus. J. Reprod. Fert. Suppl. 32:71.
Brookes, A. J. and Obyme, M., "Use of cow-heifers in beef production", J. of the Royal Agricultural Society of England 126:30. (1965).
Buchanan, B.R., et al, "Insemination of Mares with Low Numbers of Either Unsexed or Sexed Spermatozoa", Theriogenology, vol. 53, pp. 1333-1344, (2000).
Burwash, L.D., et al., 1974. Relatioship of duration of estrus to pregnancy rate in normally cycling, non-lactating mares. J.A.V.M.A. 165:714-716.
Caslick, E.A., "The Vulva and the Vulvo-vaginal Orifice and its Relation to Genital Health of the Thoroughbred Mare", Cornell Veterinarian, vol. 27, 1937, pp. 178-187.
Catt, et al., "Assesment of Ram and Boar Spermatozoa During Cell-Sorting by Flow Cytometry", Reproduction Dom Animal, vol. 32, pp. 251-258 (1997).
Catt, et al., "Birth of a Male Lamb Derived from an In Vitro Matured Oocyte Fertilized by Intracytoplasmic Injection of a Single Presumptive Male Sperm", Veterinary Record 139, 1996, pp. 494-495.
Chandler, J.E., "Videomicroscopic Comparison of Bull Sperm and Leukocyte Chromosome Areas as Related to Gender", J Dairy Sci 73, pp. 2129-2135, (1990).
Chandler, J.E., et al, "Bovine Spermatozoal Head Size Variation and Evaluation of a Separation Technique Based on this Size", Theriogeneology 52, p. 1021-1034 (1999).
Chen, Y. et al., Survival of Bull Spermatozoa Seeded and Frozen at Different Rates in Egg Yolk-Tris and Whole Milk Extenders, 1993 J Dairy Sci 76:1028-1034.
Chin, W.W. and Boime, I. 1990. In: Glycoprotein Hormones. Serona Symp. Norwell, MA. pp. 19-20.
Chung, Y.G., et al., 1998. Artificial insemination of superovulated heifers with 600,000 sexed sperm. J Anim. Sci. Suppl. 1. 836:215. abstr.

Clement, F., et al., 1998. Which insemination fertilizes when several successive inseminations are performed before ovulation. 7th Int. Symp. Eq. Repro. 151. abstr.

Cran, D.G., et al. 1997. Production of Lambs by Low Dose Intrauterine Insemination With Flow Cytometrically Sorted and Unsorted Semen, Scottish Agricultural College, UK, Theriogenology, p. 267.

Cran, D.G., et al., 1993. Production Of Bovine Calves Following Separation Of X-Chromosome and Y-Chromosome Bearing Sperm And In Vitro Fertilisation. Vet. Rec. 132:40-41.

Cran, D.G., et al., 1995. Sex preselection in cattle: a field trial. Vet. Rec. 136:495-496.

Cui, K., "Size Differences between human X and Y Spermatozoa and prefertilization diagnosis", Molecular Human Reproduction, vol. 3, No. 1, pp. 61-67, (1997).

Cui, K., "X Larger than Y", Nature 366, p. 177-118, (1993).

Curran, S. 1998. In: Equine Diagnostic Ultrasonography. Fetal gender determination. Rantanen & McKinnon. 1st Ed. Williams and Wilkins. pp. 165-169.

Day, B.N., et al., 1998. Birth of piglets preselected for gender following in vitro fertilization of in vitro matured pig oocytes by X and Y bearing spermatozoa sorted by high speed flow cytometry. Theriogenology. 49(1):360. abstr.

Dean, P.N., et al., 1978. Hydrodynamic orientation of spermatozoa heads for flow cytometry. Biophys. J. 23:7-13.

Demick, D.S., et al., 1976. Effect of cooling, storage, glycerization and spermatozoal numbers on equine fertility. J. Anim. Sci. 43:633-637.

DenDaas, J.H.G., et al., 1998. The relationship between the number of spermatozoa inseminated and the reproductive efficiency of dairy bulls. J Dairy Sci. 81: 1714-1723.

Dinnyes, A., et al., "Timing of the First Cleavage Post-insemination Affects Cryosurvival of In Vitro-produced Bovine Blastocysts", Molec Reprod develop 53, 1999, pp. 318-324.

Donaldson, L. E., "Effect of Insemination Regimen on Embryo Production in Superovulated Cows", The Veterinary Record, Jul. 13, 1985, pp. 35-37.

Donoghue, A.M., et al., 1996. Timing of ovulation after gonadotropin induction and its importance to successful intrauterine insemination in the tiger (*Panthera tigris*). J. Reprod. Fert. 107:53-58.

Douglas, R.H. 1979. Review of superovulation and embryo transfer in the equine. Theriogenology. 11:33-46.

Douglas, R.H., et al., 1974. Induction of ovulation and multiple ovulation on seasonally-anovulatory mares with equine pituitary fractions. Theriogenology. 2(6): 133-142.

Duchamp, G., et al., 1987. Alternative solutions to hCG induction of ovulation in the mare. J. Reprod. Fert. Suppl. 35:221-228.

Evans, M.J. and Irvine, C.H.G. 1977. Induction of follicular development, maturation and ovulation by gonadotropin releasing hormone administration to acyclic mares. Bio. Reprod. 16:452-462.

Fitzgerald, B.P., et al., 1993. Effect of constant administration of a gonadotropin-releasing hormone agonist on reproductive activity in mares: Preliminary evidence on suppression of ovulation during the breeding season. Am. J. Vet. Res. 54:1746-1751.

Fluharty, F.L., et al., "Effects of Age at Weaning and Diet on Growth of Calves", Ohio Agri. Res. and Dev. Circular, 1996, 156: 29.

Foote, et al. Motility and Fertility of Bull Sperm Frozen-Thawed Differently in Egg Yolk and Milk Extenders Containing Detergent, 1987 J Dairy Sci 70:2642-2647.

Foulkes, J.A., et al., 1977. Artificial insemination of cattle using varying numbers of spermatozoa. Vet. Rec. 101:205.

Francon, M. and Yamamoto, T., "Un Noveau et tres simple dispositif interferentiel applicable as microscpe", Optica Acta 9, p. 395-408 (1962).

Fugger, E.F., "Clinical Experience with Flow Cytometric Separation of Human X- and Y- Chromosome Bearing Sperm", Theriogenology, vol. 52, pp. 1435-1440 (1999).

Fulwyler, M.J. 1965. Electronic separation of biological cells by volume. Science. 150:910.

Fulwyler, M.J. 1977. Hydrodynamic orientation of cells. J Histochem. Cytochem. 25:781-783.

Garner, D.L., et al., 1983. Quantification of the X and Y chromosome-bearing spermatozoa of domestic animals by flow cytometry. Biol. Reprod. 28:312-321.

Ginther, O.J. 1971. Some factors which alter estrus cycle in mares. J. Anim. Sci. 33:1158. abstr.

Ginther, O.J. 1992. In: Reproductive Biology of the Mare. (2nd Ed.) Equiservices, Cross Plains, WI.

Gledhill, B.L. 1988. Gender preselection: historical, technical and ethical perspective. Semin Reprod. Endocrinol. 6:385-395.

Gourley, D.D. and Riese, R.L. 1990. Laparoscopic artificial insemination in sheep. Vet. Clin. N. Amer: Food Anim. Prac. 6(3):615-633.

Grondahl, C., et al, "In Vitro Production of Equine Embryos", Biology of Reproduction, Monograph Series I, pp. 299-307 (1995).

Guillou, F. and Combamous, Y. 1983. Purification of equine gonadotropins and comparative study of their acid-dissociation and receptor-binding specificity. Biochem. Biophys. Acta. 755:229-236.

Gurnsey, M.P., and Johnson, L.A., "Recent improvements in efficiency of flow cytometric sorting of X and Y-chromosome bering sperm of domestic animals: a review", 1998, New Zealand Society of Animal Protection, three pages.

Harrison, L.A., et al., 1991. Comparison of hCG, buserelin and luprostiol for induction of ovulation in cycling mares. Eq. Vet. Sci. 3:163-166.

Hawk, H.W., et al., "Fertilization Rates in Superovulating Cows After Deposition of Semen on the Infundibulum Near the Uterotubal Junction or After Insemination with High Numbers of Sperm", XP-002103478, Theriogenology, vol. 29, No. 5, pp. 1131-1142 (1988).

Hofferer, S., et al., 1993. Induction of ovulation and superovulation in mares using equine LH and FSH separated by hydrophobic interaction chromatography. J. Reprod. Fert. 98:597-602.

Holtan, D.W., et al., 1977. Estrus, ovulation and conception following synchronization with progesterone, prostaglandin F2 and human chorionic gonadotropin in pony mares. J. Anim. Sci. 44:431-437.

Householder, D.D., et al., 1981. Effect of extender, number of spermatozoa and hCG on equine fertility. J. Equine Vet. Sci. 1:9-13.

Howard, J.G., et al., 1991. Comparative semen cryopreservation in ferrets (*Mustela putorious furo*) and pregnancies after laparoscopic intrauterine insemination with frozen-thawed spermatozoa. J. Reprod. Fert. 92:109-118.

Howard, J.G., et al., 1997. Sensitivity to exogenous gonadotropins for ovulation and laparoscopic artificial insemination in the cheetah and clouded leopard. Biol. Reprod. 56:1059-1068.

Hunter, R.H.F. 1980. Transport and storage of spermatozoa in the female reproductive tract. Proc 4th Int. Congr. Anim. Repro. and A.I. 9:227-233.

Hyland, J.H., et al., 1988. Gonadotropin-releasing hormone (GnRH) delivered by continuous infusion induces fertile estrus in mares during seasonal acyclicity. Proc. Amer. Assoc. Eq. Prac. 181-190.

IMV Technologies, Protocol of Bioxcell with Fresh Semen, 1 page.

IMV Technologies, Protocol of Bioxcell with Frozen Semen, 2 pages.

Irvine, C.H.G. and Alexander, S.L. 1993. *In*: Equine Reproduction. Edited by McKinnon and Voss. Lea and Febiger. Philadelphia, London. pp. 37.

Jafar, et al., "Sex Selection in Mammals: A Review", Theriogenology, vol. 46, pp. 191-200 (1996).

Jasko, D.J., et al., "Effect of volume and concentration of spermatozoa on embryo recovery in mares", Theriogenology. 37:1233-1239, 1992.

Jasko DJ, Moran DM, Farlin ME, Squires EL, Amann RP, Pickett BW. Pregnancy rates utilizing fresh, cooled, and frozen-thawed stallion semen. Proc 38th Ann Convention AAEP 1992; 649-660.

Johnson, A.L. "Pulsatile release of gonadotropin releasing hormone advances ovulation in cycling mares", Biol. Reprod. 35:1123-1130,1986.

Johnson, A.L., et al. "Use of gonadotropin-releasing hormone (GnRH) treatment to induce multiple ovulations in the anestrous mare" Eq. Vet. Sci. 8:130-134, 1988.

Johnson, L., "Sex Preselection in Swine: Flow Cytometric Sorting of X- and Y- Chromosome Bearing Sperm to Produce Offspring", Boar Semen Preservation IV, 2000, pp. 107-114.

Johnson, L..A., "Sex Preselection in Rabbits: Live Births from X and Y Sperm Separated by DNA and Cell Sorting" Biology of Reproduction, vol. 41, pp. 199-203 (1989).

Johnson, L..A., "Advances in Gender Preselection in Swine" Journal of Reproduction and Fertility Supplement, vol. 52, pp. 255-266 (1997).

Johnson, L..A., "Sex Preselection in Swine: Altered Sex Ratios in Offspring Following Surgical Insemination of Flow Sorted X- and Y-Bearing Sperm", Reproduction in Domestic Animals, vol. 26, pp. 309-314 (1991).

Johnson, L.A. 1994. Isolation of X- and Y-bearing spermatozoa for sex preselection. *In*: Oxford Reviews of Reproductive Biology. Ed. HH Charlton. Oxford University Press. 303-326.

Johnson, L.A. 1995. Sex preselection by flow cytometric separation of X and Y chromosome bearing spermatozoa based on DNA difference: a review. Reprod. Fert. Dev. 7:893-903.

Johnson, L.A. 1997. Advances in gender preselection in swine. J Reprod. Fert. Suppl. 52:255-266.

Johnson, L.A., "Gender preselection in Mammals: An overview", Deutsch. Tierarztl. Wschr, vol. 103, pp. 288-291 (1996).

Johnson, L.A., "Flow cytometric determination of spermatozoa sex ratio in semen purportedly enriched for X or Y bearing spermatozoa" Theriogenology. 29:265. abstr.

Johnson, L.A., "Gender preselection in domestic animals using flow cytometrically sorted sperm" J Anim. Sci. Suppl 1.70:8-18. 1992.

Johnson, L.A., "The safety of sperm selection by flow cytometry" Ham. Reprod. 9(5):758, 1994.

Johnson, L.A., et al. "Sex Preselection: High-speed flow cytometric sorting of X and Y sperm for maximum efficiency", Theriogenology, vol. 52, (1999), pp. 1323-1341.

Johnson, L.A., et al., "Enhanced flow cytometric sorting of mammalian X and Y sperm: high speed sorting and orienting nozzle for artificial insemination", Theriogenology. 49(1):361. abstr., 1988.

Johnson, L.A., et al., "Flow sorting of X and Y chromosome bearing spermatozoa into two populations", Gam. Res. 16:203-212, 1987.

Johnson, L.A., et al., "Improved flow sorting resolution of X- and Y-chromosome bering viable sperm separation using dual staining and dead cell gating" Cytometry 17 (suppl 7) 83, 1994.

Johnson, L.A., et al."Modification of a Laser-Based flow Cytometer for High-Resolution DNA Analysis of Mammalian Spermatozoa", Cytometry 7, pp. 268-273 (1986).

Johnson, L.A.., "Flow sorting of X and Y chromosome-bearing sperm for DNA using an improved preparation method and staining with Hoechst" 33342. Gam. Res. 17:1-9, 1987.

Kachel, et al., "Uniform Lateral Orientation, Cused by Flow Forces, of Flat Particles in Flow-Through Systems", The Journal of Histochemistry and Cytochemistry, 1997, vol. 25, No. 7, pp. 774-780.

Kanayama, K., et al., 1992b. Pregnancy by means of tubal insemination and subsequent spontaneous pregnancy in rabbits. J. Int. Med. Res. 20:401-405.

Karabinus, et al., Effects of Egg Yolk-Citrate and Milk Extenders on Chromatin Structure and Viability of Cryopreserved Bull Sperm, 1991 J Dairy Sci. 74:3836-3848.

Kilicarslan, M.R., et al., 1996. Effect of GrnRH and hCG on ovulation and pregnancy in mares. Vet. Rec. 139:119-120.

Lapin, D.R. and Ginther, O.J. 1977. Induction of ovulation and multiple ovulations in seasonally anovulatory and ovulatory mares with an equine pituitary extract. J. Anim. Sci. 44:834-842.

Lawrenz, R. 1985. Preliminary results of non-surgical intrauterine insemination of sheep with thawed frozen semen. J S Afr. Vet. Assoc. 56(2):61-63.

Levinson, G., et al., 1995. DNA-based X-enriched sperm separation as an adjunct to preimplantation genetic testing for the preparation of X-linked disease. Mol. Human Reprod. 10:979-982.

Lindsey, A., et al., "Hysteroscopic Insemination of Mares with Nonfrozen Low-dose Unsexed or Sex-sorted Spermatozoa", currently unpublished, pp. 1-15.

Lindsey, AC, Bruemmer JE, Squires EL. Low dose insemination of mares. Animal Reproduction Science 2001; In press.

Linge, F. 1972. Faltforsok med djupfrost sperma (field trials with frozen sperm). Farskotsel. 52:12-13.

Lonergan, P., et al., "Effect of Time Interval from Insemination to First Cleavage on the Development of Bovine Embryos In Vitro and In Vivo", Theriogenology, 1999, p. 326.

Long, C.R., et al., 1998. Theriogenology. 49(1):363. abstr.

Loy, R.G. and Hughes, J.P. 1965. The effects of human chorionic gonadotropin on ovulation, length of estrus, and fertility in the mare. Cornell Vet. 56:41-50.

Macmillan, K.L. and Day, A.M., "Prostaglandin F2a : A Fertility Drug In Dairy Cattle?", Animal Research Station, Private Bag, Hamilton, New Zealand, Theriogenology, vol. 18 No. 3, pp. 245-253 (1982).

Matsuda, Y. and Tobari, I. 1988. Chromosomal analysis in mouse eggs fertilized in vitro with sperm exposed to ultraviolet light (UV) and methyl and ethyl methanesulfonate (MMS and EMS). Mutat. Res. 198:131-144.

Maxwell, W and Johnson, L. , "Chlortetracycline Analysis of Boar Spermatozoa after Incubation, Flow Cytom Sorting, Cooling, or Cryopreservation", Molecular Reproduction and Development 46, 1997, pp. 408-418.

Maxwell, W.M.C., et al., 1993. Fertility of Superovulated Ewes after Intrauterine or Oviductal Insemination with Low Numbers of Fresh or Frozen-Thawed Spermatozoa. Reprod. Fertil. Dev. 5:57-63.

Maxwell WMC, Long CR, Johnson LA,, Dorbrinsky JR, Welch GR. The relationship between membrane status and fertility of boat spermatozoa after flow cytometric sorting in the presence or absence of seminal plasma. Reprod Fertil Dev 1998; 10:433-440.

McCue, P.M. 1996. Superovulation. Vet. Clin. N. Amer. Eq. Prac. 12:1-11.

McCue, P.M., et al., 1997. Oviductal insemination in the mare. 7th Int Symp. Eq. Reprod. 133. abstr.

McDonald, L.E. 1988. Hormones of the pituitary gland. In: Veterinary Pharmacology and Therapeutics. 6th ed. Edited by N.H. Booth and L.E. McDonald. Ames, Iowa State Univ. Press. pp. 590.

McKenna, T. et al., 1990. Nonreturn rates of dairy cattle following uterine body or cornual insemination. J. Dairy Sci. 73:1179-1783.

McKinnon, A.O. and Voss, J.L. 1993. In: *Equine Reproduction*. Lea and Febiger. Philadelphia, London.

McKinnon, A.O., et al., 1993. Predictable ovulation in mares treated with an implant of the GnRH analogue deslorelin. Eq. Vet. J. 25:321-323.

McKinnon, A.O., et al., 1996. Repeated use of a GnRH analogue deslorelin (Ovuplant) for hastening ovulation in the transitional mare. Eq. Vet. J. 29:153-155.

McNutt, et al., "Flow Cytometric Sorting of Sperm: Influence on Fertilization and Embryo/Fetal Development in the Rabbits", Molecular Reproduction and Development, vol. 43, pp. 261-267 (1996).

Meinert, C., et al., "Advancing the time of ovulation in the mare with a short-term inplant releasing the GnRH analogue deslorelin", Equine Veterinary Journal, 25, pp. 65-68 (1993).

Merton, J., et al., "Effect of Flow Cytometrically Sorted Frozen/Thawed Semen on Success Rate of In Vitro Bovine Embryo Production", Theriogenology 47, 1997, p. 295.

Meyers, P.J., et al., 1997. Use of the GnRH analogue, deslorelin acetate, in a slow release implant to accelerate ovulation in oestrous mares. Vet. Rec. 140:249-252.

Michaels, Charles, "Beef A.I. Facilities that work", Proc. Fifth N.A.A.B Tech. Conf. A.I. Reprod. Columbia, MO. pp. 20-22.

Michel, T.H., et al., 1986. Efficacy of human chorionic gonadotrophin and gonadatrophin releasing hormone for hastening ovulation in Thoroughbred mares. Eq. Vet. J. 6:438-442.

Miller, S.J. 1986. *Artificial Breeding Techniques in Sheep*. In Morrow, D.A. (ed): Current Therapy in Theriogenology 2. Philadelphia, WB Saunders.

Mirskaja, L.M. and Petrapavlovskii, V.V. 1937. The reproduction of normal duration of heat in the mare by the administration of Prolan. Probl. Zivotn. Anim. Breed. Abstr. 5:387.

Molinia, F.C., et al., 1998. Successful fertilization after superovulation and laparoscopic intrauterine insemination of the brushtail possum, *Trichosurus vulpecula*, and tammar wallaby, *Macropus eugenii*. J.Reprod. Fert. 112:9-17.

Moran DM, Jasko, DJ, Squires EL, Amann RP. Determination of tempature and cooling rate which induce cold shock in stallion spermatozoa. Theriogenology 1992; 38:999-1012.

Morcom, C.B. and Dukelow, W.R. 1980. A research technique for the oviductal insemination of pigs using laparoscopy. Lab. Anim. Sci. 1030-1031.

Morris, L.H., et al., "Hysteroscopic insemination of small numbers of spermatozoa at the uterotubal junction of preovulatory mares", Journal of Reproduction and Fertility, vol. 118, pp. 95-100 (2000).

Muller, W. and Gautier, F. 1975. Interactions of heteroaromatic compounds with nucleic acids. Euro. J Biochem. 54:358.

Munne, S. 1994. Flow cytometry separation of X and Y spermatozoa could be detrimental to human embryos. Hum. Reprod. 9(5):758.

Nowshari, et al., "Superovulation of Goats with Purified pFSH Supplemented with Defined Amounts of pLH", Theriogenology, vol. 43, pp. 797-802 (1995).

Pace, M.M. and Sullivan, J.J. 1975. Effect of timing of insemination, numbers of spermatozoa and extender components on pregnancy rates in mares inseminated with frozen stallion semen. J Reprod. Fert. Suppl. 23:115-121.

Parrish, J.J. "Capacitation of Bovine Sperm by Heparin", Department of Meat and Animal Science, Biology Of Reproduction 38, pp. 1171-1180 (1988).

Peippo, J., et al., "Sex diagnosis of equine preimplantation embryos using the polymerase chain reaction", Theriogenology, vol. 44 619-627 (1995).

Penfold, L.M. et al., "Comparative Motility of X and Y Chromosome-Bearing Bovine Sperm Separated on the Basis of DNA Content", Mol. Reprod. and Develop. 1998, vol. 50, pp. 323-327.

Perry, E.J. 1968. Historical Background In: *The Artificial ]nsemination of Farm Animals*. 4th ed. Edited by E.J. Perry. New Brunswick, Rutgers University Press, pp. 3-12.

Petersen, G.A., et al, "Cow and Calf Performance and Economic Considerations of Early Weaning of Fall-Born Beef Claves", J. Anim. Sci., 1987, 64:15, pp. 15-22.

Pickett, B.W, et al., 1976. Factors influencing the fertility of stallion spermatozoa in an A.I. program. Proc. 8th Internat. Congr. Anim. Reprod. A.I. Krakow, Poland. 4: 1049-1052.

Pickett, B.W. and Back, D.G. 1973. Procedures for preparation, collection, evaluation and insemination of stallion semen. C.S.U. Exp. Sta. Artira. Reprod. Lab. Gen. Series Bull. 935.

Pickett, B.W., and Shiner, K.A., "Recent developments in artificial insemination in horses", Livestock Production Science, 40, pp. 31-36 (1994).

Pickett, B.W., et al., 1974. The effect of extenders, spermatozoal numbers and rectal palpation on equine fertility. Proc. Fifth N.A.A.B Tech. Conf. A.I. Reprod. Columbia, MO. pp. 20-22.

Pickett, B.W., et al., 1975b. Effect of seminal extenders on equine fertility. J. Anim. Sci. 40:1136-1143.

Pickett, B.W., et al., 1978. Influence of seminal additives and packaging systems on fertility of bovine spermatozoa. J. Anim. Sci. Suppl. II. 47:12.

Pickett, B.W., et al., 1989. Management of the mare for maximum reproductive efficiency. C.S.U. Anim. Repro. Lab. Bull. No. 06. Fort Collins CO.

Pinkel, D., et al, "Flow Cytometric Determination of the Proportions of X- and Y- Chromosome-Bearing Sperm in Samples of Purportedly Separated Bull Sperm", Journal of Animal Science, vol. 60, pp. 1303-1307 (1998).

Pinkel, D., et al., 1982b. High resolution DNA measurements of mammalian spermatozoa. Cytometry. 3:1-9.

Province CA, Squires EL, Pickett BW, Amann RP. Cooling rates, stroage temperatures and fertility of extended equine spermatozoa. Theriogenlolgy 1985; 23:925-934.

Rath, D., et al., "Low Dose Insemination Technique in the Pig", Boar Semen Preservation IV, 2000, pp. 115-118.

Rath, D., et al., "Production of Piglets Preselected for Sex Following in Vitro Fertilization with X and Y Chromosome-Bearing Spermatozoa Sorted by Flow Cytometry", Theriogenology, 47, pp. 795-800 (1997).

Rathi, R. et al., "Evaluation of In Vitro Capacitation of Stallion Spermatoza", Biology of Reproduction 2001, vol. 65, pp. 462-470.

Reiling, B.A., et al., "Effect of Prenatal Androgenization on Preformance, Location, and Carcass and Sensory Traits on Heifers in Single Calf Heifer System", J. Anim. Sci., 1995, 73: 986, pp. 986-992.

Rens, W., et al., "A Novel Nozzle for More Efficient Sperm Orientation to Improve Sorting Efficiency of X and Y Chromosome-Bearing Sperm", Technical Notes, Cytometry 33, 1998, pp. 476-481.

Rens, W., et al., "Improved Flow Cytometric Sorting of X- and Y-Chromosome Bearing Sperm: Substantial Increase in Yield of Sexed Semen", Molecular Reproduction and Development, 1999, pp. 50-56.

Rieger, D., et al, "The Relationship Between the Time of First Cleavage of Fertilized Cattle Oocytes and Their Development to the Blastocyst Stage", Theriogenology, 1999, pp. 190.

Rigby SL, Lindsey AC, Brinsko SP, Blanchard TL, Love CC, Varner DD. Pregnancy rates on mares following hysteroscopic or rectally-guided utero-tubal insemination with low sperm numbers. Proc $3^{rd}$ International Symposium on Stallion Reproduction 2001; 49 (abstr.).

Ritar, A. and Ball, A. 1991. Fertility of young cashmere goats after laparoscopic insemination. J. Agr. Sci. 117:271-273.

Roberts, J.R. 1971. In: Veterinary Obstetrics and Genital Diseases. Ithaca, New York. pp. 740-749.

Roser, JF., et al., 1980. Reproductive efficiency in mares with anti-hCG antibodies. Proc 9th Int. Congr. Anim. Repro. and A.I. 4:627. abstr.

Roth, T.L., et al., 1997. Effects of equine chorionic gonadotropin, human chorionic gonadotropin, and laparoscopic artificial insemination on embryo, endocrine, and luteal characteristics in the domestic cat. Bio Reprod. 57:165-171.

Rowley, H-S., et al., 1990. Effect of insemination volume on embryo recovery in mares. J. Equine Vet. Sci. 10:298-300.

Salamon, S. 1976. Artificial Insemination of Sheep. Chippendale, New South Whales. Publicity Press. p. 83-84.

Salisbury, G.W. and VanDemark, N.L. 1961. Physiology of Reproduction and Artificial Insemination of Cattle. San Francisco: Freeman and Company.

SAS, SAS/STAT® User's Guide (Release 6.03), SAS Inst. Inc., Cary, NC., 1988.

Schenk, J.L., "Cryopreservation of flow-sorted bovine spermatozoa", Theriogenology, vol. 52, 1375-1391 (1999).

Schenk, J.L. and Seidel, Jr., G.E., "Imminent Commercialization of Sexed Bovine", Proceedings, The Range Beef Cow Symposium XVL, 1999, pp. 89-96.

Schenk, J. L. et al., Unpublished Document, Insemination of Holstein Heifers with sexed Sperm Processed withor without Egg Yolk-Tris-Glycerol-Containing Medium.

Schenk,J. L., Unpublished Document, Introduction: The role of Egg yolk in the sperm cryopreservation medium has been well documented.

Schenk, J. L., Unpublished Document, Comparison of Different Egg Yolk-Fractions for Cooling and Freezing Sorted Bovine Sperm, Dec. 23, 2004.

Schenk, J. L., Unpublished Document, First Results No Egg Yolk.

Schmid R.L., et al, "Fertilization with Sexed Equine Spermatozoa Using Intracytoplasmic Sperm Injection and Oviductal Insemination", 7th International Symposium On Equine Reproduction, pp. 139 (Abstract) (1998).

Seidel, G. Jr., "Use of Sexed Bovine Sperm for In Vitro Fertilization and Superovulation", Animal Reproduction and Biotechnology Laboratory, Colorado State University, Proceedings of the 2000 CETA/ACTE Convention, Charlottetown, Prince Edward Island, Aug. 2000, pp. 22-24.

Seidel, G.E. Jr, et al., "Artificial Insemination of Heifers with Cooled, Unfrozen Sexed Semen ", Theriogenology, vol. 49 pp. 365 (Abstract) (1998).

Seidel, G.E. Jr, et al., "Insemination of Heifers with Sexed Sperm", Theriogenology, vol. 52, pp. 1407-1421 (1999).

Seidel, G.E. Jr., "Uterine Horn Insemination of Heifers With Very Low Numbers of Nonfrozen and Sexed Spermatozoa", Atlantic Breeders Cooperative, Theriogenology 48: pp. 1255-1264, (1997).

Seidel, G.E. Jr., et al., 1998. Artificial insemination of heifers with cooled, unfrozen, sexed semen. 1998. Theriogenology. 49(1):365. abstr.

Seidel, G.E. Jr.,et al., 1999. Insemination of heifers with sexed frozen or sexed liquid semen. Theriogenology. 51. (in press). abstr.

Seidel, G.E., "Status of Sexing Semen for Beef Cattle", Texas A&M University 45th Annual Beef Cattle Short Course and Trade Show Proceedings, Aug. 9-11, 1999; pp. III 24-III 27.

Seidel, Jr., G. E., "Artificial Insemination With X-and Y-Bearing Bovine Sperm", Animal Reproduction and Biotechnology Laboratory, Colorado State University, (1996).

Seidel, Jr., G. E., et al, "Insemination of Holstein Heifers With Very Low Numbers Of Unfrozen Spermatozoa", Colorado State University, Atlantic Breeders Cooperative, (1995).

Seidel, Jr., G.E.et al, "Insemination Of Heifers With Very Low Numbers Of Frozen Spermatozoa", Colorado State University (1996).

Senger, P.L., et al., 1988. Influence of cornual insemination on conception rates in dairy cattle. J Anim Sci. 66:3010-3016.

Shelton, J.N. and Moore, N.W. 1967. The response of the ewe tot pregnant serum mare gonadotropin and to horse anterior pituitary extract. J. Reprod. Fert. 14:175-177.

Shilova, A.V., et al., 1976. The use of human chorionic gonadothrophin for ovulation date regulation in mares. VIIIth Int. Congr. On Anim. Repro. and A.I. 204-208.

Smith, R. L., et al, Influence of Percent Egg Yolk during Cooling and Freezing on Survival of Bovine Spermatozoa, Dairy Science 1979 J 62:1297-1303.

Squires, E., "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, pp. 127-130 (1996).

Squires, E.L, et al., 1994. Effect of dose of GnRH analogue on ovulation in mares. Theriogenology. 41:757-769.

Squires, E.L., "Early Embryonic Loss" in Equine Diagnostic Ultrasonography, $1^{st}$ Ed. pp. 157-163 Eds Rantanen & McKinnon. Williams and Wilkins, Baltimore, Maryland (1998).

Squires, E.L.., et al, "Cooled and frozen stallion semen", Bulletin No. 9, Colorado State University, Ft. Collins, CO. (1999).

Sullivan, J.J., et al., 1973. Duration of estrus and ovulation time in nonlactating mares given human chorionic gonadotropin during three successive estrous periods. J.A.V.M.A. 162:895-898.

Sumner, A.T. and Robinson, J.A., "A Difference in Dry mass between the heads of X and Y-bearing human Spermatozoa", J Reprod Fert 48, p. 9-15(1976).

Taljaard, T.L., et al., 1991. The effect of the laparoscopic insemination technique on the oestrus cycle of the ewe. J. S Afr. Vet. Assoc. 62(2):60-61.

Taylor, C.S., "Efficiency of Food Utilization in Traditional and Sex-Controlled Systems of Beef Production", AFRC Animal Breeding Research Organization, West Mains Road, Edinburg EH9 3JQ, pp. 401-440.

Tervit, H.R., et al., "Successful Culture In Vitro of Sheep and Cattle Ova", Agricultural Research Council, Unit of Reproduction Physiology and Biochemistry, University of Cambridge, 1972, p. 493-497.

Thun, Rico, et al., Comparison of Biociphos-Plus® and TRIS-Egg Yolk Extender for Cryopreservation of Bull Semen; Theriogenology Symposium, Dec. 1999, vol. 52, #8.

Van Munster E.B., et al, "Difference in Volume of X- and Y-chromosome Bearing Bovine Sperm Heads Matches Difference in DNA Content" Cytometry 35 p. 125-128 (1999.

Van Munster E.B., et al, "Measurement-based evaluation of optical pathlength distributions reconstructed from simulated differential interference contrast images", Journal of Microscopy 192, Pt. 2, p. 170-176 (1998).

Van Munster, E.B., "Geslachtsbepaling met interferometrie", Derde prijs NtvN-prijsvraag voor pas-gepromoveerden 65/4, p. 95-98 (1999).

Van Munster, E.B., et al, "Difference in Sperm Head Volume as a Theoretical Basis for Sorting X & Y-Bearing Spermatozoa: Potentials and Limitations", Theriogenology 52, pp. 1281-1293, (1999).

Van Munster, E.B., et al, "Reconstruction of optical pathlength distributions form images obtained by a wide field differential interference contrast microscope", Journal of Microscopy 188, Pt. 2, p. 149-157 (1997).

Vazquez, J. et al., "Nonsurgical Uterotubal Insemination in the Mare", Proceedings of the 44th Annual Convention of the American Association of Equine Practitioners, vol. 44, pp. 68-69 (1998).

Vazquez, J., et al., "A.I. in Swine; New Strategy for Deep Insemination with Low Number of Spermatozoa Using a Non-surgical Methodology", $14^{th}$ International Congress on Animal Reproduction, vol. 2, Stockhlom, Jul. 2000, p. 289.

Vazquez, J., et al., "Successful Low-Dose Insemination by a Fiberoptic Endoscope Technique in the Sow", Proceedings Annual Conference of the International Embryo Transfer Society, Netherlands, Theriogenology, vol. 53, Jan. 2000, pp. 201.

Vazquez, J., et al.,"Development of a Non-surgical Deep Intra Uterine Insemination Technique", Boar Semen Preservation IV, IVth International Conference on Boar Semen Preservation, Maryland, pp. 262-263.

Vazquez, J., et al.,"Hypoosmotic Swelling Test as Predictor of the Membrane Integrity in Boar Spermatozoa", Boar Semen Preservation IV, IVth International Conference on Boar Semen Preservation, Maryland, pp. 263.

Vidament, M., et al., 1997. Equine frozen semen freezeability and fertility field results. Theriogenology. 48:907.

Vogel, T., et al, "Organization and expression of bovine TSPY", Mammalian Genome, vol. 8, pp. 491-496 (1997).

Voss, J.L. and Pickett, B.W. 1976. Reproductive management of the broodmare. C.S.U. Exp. Sta. Anim. Reprod. Lab. Gen. Series. Bull. 961.

Voss, J.L., et al., 1974. Effect of human chorionic gonadotropin on duration of estrous cycle and fertility of normally cycling, nonlactating mares. J.A.V.M.A. 165:704-706.

Voss, J.L., et al., 1982. Effect of number and frequency of inseminations on fertility in mares. J. Reprod. Fertil. Suppl. 32:53-57.

Welch G.R., et al., 1994. Fluidic and optical modifications to a FACS IV for flow sorting of X- and Y- chromosome bearing sperm based on DNA. Cytometry 17 (suppl. 7): 74.

Welch, G., et al., "Flow Cytometric Sperm Sorting and PCR to Confirm Separation of X- and Y- Chromosome Bearing Bovine Sperm", Animal Biotechnology, 6, pp. 131-139 (1995).

Wilson, C.G., et al., 1990. Effects of repeated hCG injections on reproductive efficiency in mares. Eq. Vet. Sci. 4:301-308.

Wilson, M.S. 1993. Non-surgical intrauterine artificial insemination in bitches using frozen semen. J.Reprod. Fert Suppl. 47:307-311.

Windsor, D.P., et al, "Sex Predetermination by Seperation of X and Y Chromosome-bearing Sperm: A Review", Reproduction of Fertilization and Developement 5, pp. 155-171, (1993).

Woods, J. and Ginther, O.J. 1983. Recent studies related to the collection of multiple embryos in mares. Theriogenology. 19:101-108.

Woods, J., et al., 1990. Effects of time of insemination relative to ovulation on pregnancy rate and embryonic-loss rate in mares. Eq. Vet. J. 22(6):410-415.

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Asbury, Charles A. "Fluorescence Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beer", J. Anim. Sci. 69:1403. (1991).

Bakker Schut, Tom C. "A New Principle of Cell Sorting by Using Selective Electroportation in a Modified Flow Cytometry," University of Twente, Mar. 10, 1990.

Behrman, S. J., et al., "Freeze Preservation of Human Sperm" American Journal of Obstetrics and Gynecology vol. 103 (5) p. 654-664 Mar. 1, 1969.

Bellows, R. A., et al., "Cause and Effect Relationships Associated With Calving Difficulty and Calf Birth Weight", J. Anim. Sci. 33:407. (1971).

Berardinelli, J. G., et al., "Source of Progesterolle Prior to Puberty in Beef Heifers". J. Anim. Sci. 49:1276. (1979).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Bigos, Martin "Nine Color Eleven Parameter Immunophenotyping Using Three Laser Flow Cytometry," Stanford University Dec. 22, 1998.

Bond, J., et al., "Growth and Carcass Traits of Open Beef Heifers Versus Beef Heifers That Have Calved", Nutrition Reports International 34:621. 1986.

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef-Production III. Culling Strategies and Nontraditional Management-Systems", J. Anim. Sci. 65:963. 1987.

Braun, J. et al, "Effect of Different Protein Supplements on Motility and Plasma Membrane Integrity of Frozen- Thawed Stallion Spermatozoa", Cryobiology (1995) 32:487-492.

Buchanan, B.R. "Pregnancy Rates in Mares Following a Single Insemination with a Low Number of Spermatozoa into the Tip of the Uterine Horn" Theriogenology p. 395 1999.

Burns, P. D. and Spitzer, J.C., "Influence of Biostimulation on Reproduction in Postpartum Beef-Cows", J. Anim. Sci. 70:358. 1992.

Byerley, D. J., et al., "Pregnancy Rates of Beef Heifers Bred Either on Puberal or Third Estrus". J Anim. Sci. 65:645. 1987.

Cave-Penney, Tony, "Sexed Semen Offers Faster Genetic Gain", Farming News, Livestock Supplement, Feb. 1997, p. 28.

Celestron: Telescope Basics: www.celestron.com/tb-2ref/htm; 4 pages, Oct. 20, 2003.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Choi, Y.H. "Developmental Cappacity of Equine Oocytes Matured and Cultured in Equine Trophoblast-Conditioned Media" Theriogenoogy 56: 320-339, 2001.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. of Aberdeen, Scotland. 1973.

da Silva, Coutinho M.A.."Effect of time of oocyte collection and site of insemination on oocyte transfer in mares." Animal Reproduction and Biotechnology Laboratory, Colorado State Uniuversity, Fort Collins Journal of Animal Science 2002. 80:1275-1279.

DakoCytomation, "MoFlo® Sorters" http://www.dakocytomation.us/prod_productrelatedinformation?url=gprod_moflo_index.htm one page, printed Jun. 26, 2003.

Database up 1 BR9704313 (Alves, De Resende et al) Jun. 4, 1999.

de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

Diagnostic Products Corporation, "Coat-A-Count" http://www.Progesterone.com. 1998.

Dikeman, M. E. "Cattle Production Systems to Meet Future Consumer Demands" J. Anim. Sci. 59:1631, 1984.

Dippert, K.D. "Fertilization Rates in Superovulated and Spontaneously Ovulating Mares" Theriogenology 41: 1411-1423, 1994.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analysis of DNAcontent ofLiving Spermatozoa Using Flow Cytometry Technique Journal of Reproduction and Fertility, 1993, vol. 98, pp. 357-365.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Foote, R.H., "Buffers and Extenders: What Do They Do? Why Are They Important?" Proc of the NAAB Tech. Conf. On Artificial Insemination and Reproduction, 62-70 (1984).

Fuller, Robert R. "Characterizing Submicron Vesicles With Wavelenth-Resolved Fluorescence in Flow Cytometry," University of Illinois, May 13, 1996.

Ginther, O. J., "Sexual Behavior Following Introduction of a Stallion into a Group of Mares" Therio. vol. 19 Jun. 6, 1983.

Gombe, S. and Hansel, W. "Plasma Luteinizing Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper—Mayer"; Zbechr. F. Phys. 47 S. 509 1928.

Gottlinger et al., "Operation of a Flow Cytometer", Flow Cytometry and Cell Sorting, A. Radbruch (Ed.), 1992, pp. 7-23.

Graham, J. Analysis of Stallion semen and its Relation to Fertility. Abstract Complete article from Reproductive Technology vol. 12 # Apr. 1, 1996 now included in XYIDS000213.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal Weaned Calves". I. Prod. Agric. 4:168 (1991).

Hall, J. B., et al., "Effect of Age and Pattern of Gain on Induction of Puberty with a Progestin in Beef Heifers." J. Anim. Sci. 75:1606 (1997).

Hamamatsu, "*Technical Information, Optical Detector Selection; A Delicate Balancing Act*", web page, http://www.optics.org/hamamatsu/photodiode.html, printed on Apr. 15, 2000, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harte, F. J. "System of Production of Beef From Once Calved Heifers." In: J.C. Taylor (Ed.) *The Early Calving of Heifers and its Impact on Beef Production.* 123 (1975).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," Sci. Am. 1976; 234, pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hohenboken, W. D. "Applications of sexed semen in cattle production." Therio. 52:1421. 1999.

Horan, Paul K. "Quantitative Single Cell Ana,lysis and Sorting, Rapid Analysis and sorting of cells is emerging as an important new technology in research and medicine." Science, Oct. 1977.

Howard, J. G., et al., "Comparative Semen Cryopreservation in Ferrets (*Mustela putorious furo*) and Pregnancies After Laparoscopic Intrauterine Insemination With Frozen-Thawed Spermatozoa." J. Reprod. Fertil. 92:109-118. 1991.

Iwazumi, Y., et al., "Superovulation Using CIDR in Holstein Cows" J. of Reprod. Dev. vol. 40 (3) 1994, pp. 259-266.

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production.* 10. (1975).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Successful Gender Preselection in Farm Animals", Agricultural Biotechnology, p. 439-452. (1998).

Joseph, R. L. "Carcass composition and meat quality in once calved heifers." In: J.C. Taylor (Ed.) *The Early Calving of Heifers and its Impact on Beef Production.* 143. (1975).

Joseph, R. L. and J. P. Crowley. "Meat Quality of Once-Calved Heifers." Irish J. of Agric. Research 10:281. (1971).

Keeling, P. "A Modeling Study of Once-Bred Heifer Beef Production." Proceedings of the New Zealand Society of Animal Production. 51. (1991).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20, 1990.

Koch, R. M., et al., "Characterization of Biological Types of Cattle -Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Laster, D. B., "Factors Affecting Dystocia and Effects of Dystocia on Subsequent Reproduction in Beef-Cattle." J. Anim. Sci. 36:695. (1973).

Lightwave Electronics, "Xcyte," www.LightwaveElecronics.com.

Liu, Z, et al. "Survival of Bull Sperm Frozen at Different rates in Media Varying in Osmolarity." Cryobiology, vol. 27, 1998, pp. 219-230.

Lu, K. H. et al., "In Vitro Fertilization of Bovine Oocytes with Flow-Cytometrically Sorted and Unsorted Sperm from Different Bulls" Therio. 2001 abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Manni, Jeff. "To-Photon Excitation Expands the Capabilities of Laser-Scanning Microscopy," 1996 Biophotonics International.

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow ", Proceedings Annual Conference of the International Embryo Transfer Society, Netherlands, Therio. vol. 53 p. 201, Jan. 2000.

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calving of Heifers and its Impact on Beef Production.* (1975).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

Meilgaard, M., et al., "Sensor Evaluation Techniques." CRC Press Inc., Boca Raton, FL. (1991).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991 ,vol. 30 pp. 250-257.

Moe, P. W., "Energetics of Body Tissue Mobilization." J. of Dairy Sci. 1971 54:548.

Moran, C., et al., "Puberty in Heifers -a Review." Animal Reproduction Sci. 18:167. (1989).

Morgan, J. B., et al., "National Beef Tenderness Survey." J. Anim. Sci. 69: 3274. (1991).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001 (Suppl. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, lzdatelstvo Selskokhozyaastvennoi Literatury, 1961, pp. 350-361 and pp. 380-393.

Patterson, D. J., et al., "Estrus Synchronization with an Oral Progestogen Prior to Superovulation of Postpartum Beef Cows" Therio. 48, 1025-33 (1997).

Petit, M. "Early Calving in Suckling Herds." In: J.C. Taylor (ed.) *The Early Calving of Heifers and its Impact on Beef Production*. p. 157-176. (1975).

Picket B.W., et al., "Livestock Production Science," 1998.

Pinkel et al., "Flow Chambers and Sample Handling", Flow Cytometry: Instrumentation and Data Analysis, Van Dilla et al. (Eds.), 1985, pp. 77-128.

Pinkel, D., et al., "Sex Preselection in Mammals? Separation of Sperm Bearing the Y and "O" Chromosomes in the Vole *Microtus oregoni*", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, NAOUKA Publishing House, 1983, pp. 181-195.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Recktenwald, Diether. "Cell Separation Methods and Applications," New York 1997.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (1996).

Riggs, B.A. "Integration of Early Weaning and Use of Sexed Semen in a Single-Calf Heifer System to Increase Value of Non-Replacement Heifers" MS Thesis, Colorado State University, Spring 2000.

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production*. 23. (1975).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Roy, J. H., "Rearing Dairy-Herd Replacements." Journal of the Society Of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Schiewe, M. C., et al., "Transferable Embryo Recovery Rates Following Different Insemination Schedules in Superovulated Beef Cattle" Therio. 28 Oct. 4, 1997, pp. 395-406.

Schillo, K. K., et al, "Effects of Nutrition and Season on the Onset of Puberty in the Beef Heifer." J. Anim. Sci. 70:3994 (1992).

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34, Sep. 2001.

Seidel, G. E. Jr. Sexing mammalian spermatozoa and embryos-state of the art Journal of Reproduction and Fertility Supp 54, 477-487 1999.

Seidel, G. E. Jr et al., "Current Status of Sexing Mammalian Spermatozoa," Society for Reproduction and fertiity, pp. 733-743, 2002.

Seidel, G. E. Jr., "Commercilizing Repreductive Biotechnology—The Approach used by XY, Inc.," Theriogenology, p. 5, 1999.

Seidel, G. E. Jr., et al, "Sexing Mammalian Sperm—Overview", Therio. 52: 1267-1272, (1999).

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.; Oct. 1988.

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997, Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Solsberry G.U., Van-Denmark N.L., Theory and practice of artificial cow insemination in USA, Moscow, Kolos Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HMD 532, www.specra-physics.com, Copyright 2002.

Spectra-Physics, The Solid State Laser Company, Vanguard 350-HMD 355, www.specra-physics.com Copyright 2002.

Squires, E.L., "Procedures for Handling Frozen Equine Semen for Maximum Reproductive Efficiency", (1998) pp. 1, 39-41, 81-89.

Staigmiller, R.B. "Superovulation of Cattle with Equine Pituitary Extract and Porcine FSH" Theriogenology 37: 1091-1099 1992.

Stap J. et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments, Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Swanson, E. W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Tatum, J. D., et al., "Carcass Characteristics, Time on Feed and Cooked Beef Palatability Attributes." J. Anim. Sci. 50:833. (1980).

*Time-Bandwidth Products* "GE—100—XHP", www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

Vincent, B.C., et al, "Carcass Characteristics and Meat Quality of Once-Calved Heifers." Canadian J. Anim. Sci. 71:311. (1991).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservvation of Spermatozoa and the Assessment of Their Post-Thawing Function," Reprod. Fertil. Dev. 7:871-891 (1995) Abstract.

Wheeler, T. L., et al., "Effect of Marbling Degree on Beef Palatability in Bos-taurus and Bos-indicus cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, D. E. et al., "Mammal Species of the World", Smithsonian Institution Press, 1993, 1206 pp.

Wintzer et al.:"Krankheiten des Pferdes Ein Leitfaden fur Studium und Praxiz," 1982, nParey, Berlin Hamburg XP002281450.

Zhou, Hongwei, et al. "Research on and Development of Flow Cell Sorting Apparatuses," Gazette of Biophysics, vol. 13, ed. 3, 1997.

Hamamatsu, "*Photomultiplier Tubes*," web page, http://www.optics.org/hamamatsu/pmt.html. Printed on Apr. 15, 2000 4.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23, (1995).

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.

Hollinshead F. K. et al. "Production of lambs of predetermined sex after the insemination of ewes with low numbers of frozen-thawed sorted X- or Y- Chromosome-bearing spermatozoa", Reprod. Fertil. And Develop. 2002, vol. 14, pp. 503-508.

Hollinshead F. K. et al. "Sex-Sorting and Re-cryopreservation of Frozen-Thawed Ram Sperm for In Vitro Embryo Production" Theriogenology , vol. 59. (2003) pp. 209.

Dhali et al. Vitrification of Buffalo (*Bubalus bubalis*)Oocytes, Embryo Theriogenology vol. 53, pp. 1295-1303 (2000).

Borini et al. Cryopreservation of Mature Oocytes: The use of a trypsin inhibitor enhances fertilization and obtained embryos rates, Fertil. Steril. (1997), vol. 68 (Suppl.).

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for In Vitro fertiliation and AI, Journal of Animal Science,vol. 77, Suppl 2/J, Dairy Sci. vol. 82, Suppl. Feb. 1999 pp. 213-220.

Peters D., The LLNL high-speed sorter: Design features,operational characteristics, and bioloical utility, Cyometry, 6:290-301 (1985).

Rens W., et al Slit-scan flow cytometry for consistent high resdolution DNA analysis of X- and Y- chromosome bearing sperm, Cytometry 25:191-199 (1996).

van Munster, E. B. Interferometry in flor to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/lsrll.htm, pp. 14, May 11, 2004.

Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.

Blecher, S.R., et al. A new approach to immunological sexing of sperm, Theriogenology, 59, pp. 1309-1321, 1999 Vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen recepters (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, 65 (2006) 943-957.

Habermann F. A., et al., Validation of sperm sexing in the cattle (*Bos taurus*) by dual colour flourescence in situ hybridization; J Anim Breed Genet. Apr. 2005; 122 Suppl 1:22-7 (Abstract only).

Johnson, L. A., Sexing mammalian sperm for production of offspring: the state-of-the-art; Animal Reproduction Science; 60-61 (2000) pp. 93-107.

Seidel, G.E. Jr., et al., Methods of Ovum Recovery and Factors Affecting Fertilization of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, T. et al., Milk Production Evaluation In First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Dairy Industry $in Asia B. Japan; www.agnet.org/library/article/eb384b.html.

Lopez, H. et al., Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology (1998) www.foodsci.uoguelph.ca/dairyedu/biosyntheses.html.

Milk Production, Released Jul. 18, 2006, by the National Agricultural Statistics Service (NASS), Agri. Stats. Board, US Dept of Agri.

DeVries, A. Economic Value of Pregnancy in Dairy Cattle Journal of Dairy Sci. 89:3876-3885/American Dairy Sci. Assoc. 2006.

Garner, D.L. et al., Viability Assessment of Mammalian Sperm Using SYBR-14 and Propidium Lodide, 1996, Biology of Reporduction, vol. 53, pp. 276-284.

Salisbury, G.W. et al., Substrate-Free Epididymal-Like Bovine Spermatozoa, J Repord Fertil, 1963, vol. 6, pp. 351-359.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel Anguilla Japonica, National Research Institute of Aquaculture, UNJR Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa , School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, September/October 616-624.

Jenkins, A. D., et al. Concentrations of Seven Elements in the Intraluminal Fluids of the Rat Seminiferous Tubules, Rete Testis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and β-D-Glucuron idase Activity as Indicators of Sea Bass Semen Quality; Biology of Reproduction 70, 1679-1684 (2004) Published online before print Feb. 11, 2004.

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Bavister, B.D. et al., The effects of Sperm Extracts and Energy Sources on the Motility and Acromosome Reaction of hamster Spermatozoa in vitero; Biology of Reproduction 16, 228-237 (1997).

Fattouh, EI-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals; Journal of Andrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130; 2004 American Dairy Science Assoc.

Arathy D.S., et al., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number of Accessory Sperm, Fetilization Rate, and Embryo Quality in Nonlactating Dairy Cattle. J Dairy Sci. 84:2413-2418.

Dransfield, M.B.G., et al., Timing of Inseminatio for Dairy Cows Identified in Estrus by a Radiotelemetric Etrus Detection System. 1998 J Dairy Sci. 81: 1874-1882.

Maatje, K. et al. Predicting Optimal Time of Insemination in Cows that Show Visual Signs of Estrus by Estimating onset of Estrus with Pedometers.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Size in Swine J. Animal Sci. 1997. 75: 2323-2327.

Peeler, I. D. et al. Pregnancy Rates After Times AI of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (*Anser anser* L.) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conley, H.H. et at. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Bakst, Murray R. Fate of Fluorescent Stained Sperm following Insemination: New Light on Ovicucal Sperm Transport and Storage in the Turkey.

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

* cited by examiner

METHODS AND APPARATUS FOR REDUCING PROTEIN CONTENT IN SPERM CELL EXTENDERS

This is a United States non-provisional patent application and claims priority to U.S. Provisional Application No. 60/704,001, filed Jul. 29, 2005, hereby incorporated herein by reference.

BACKGROUND OF THE INVENTION

Generally, the inventive technology disclosed herein relates to methods and apparatus for reducing protein content in sperm cell extenders. More specifically, this inventive technology may involve eliminating the protein content of a cryoprotectant component used in a multiple step sperm cell extension process. The inventive technology may be particularly suited for use in sorted sperm applications.

Sperm cell extenders may be commonly used in a variety of biological disciplines that require working with sperm cells. For example, one discipline that may make extensive use of sperm cell extenders is the field of artificial insemination. Whereas natural insemination may involve direct male to female insemination, artificial insemination may typically involve collecting sperm cells from a male, performing a degree of human manipulation of such sperm cells removed from their natural environment, and then inserting the manipulated sperm cells into a female. The precise degree of human manipulation may vary depending on the precise nature of the particular application. For example, some human manipulation may simply involve dividing a collected sperm sample into multiple doses for use in multiple insemination events, possibly with multiple female animals. However, other applications may require more intensive human manipulation.

For example, human manipulation in some applications may involve sorting sperm cells into populations based on characteristics exhibited by sperm cells. One such application may include the use of flow cytometery to separate sperm cells into populations of X-chromosome-bearing and Y-chromosome bearing sperm cells. A flow cytometer may typically accomplish such separation by flowing sperm cells entrained in a fluid stream one at a time through an interrogation region, where information about each sperm cell may be obtained. Interrogation may typically be accomplished through the use of optics, for example perhaps by intersecting a laser beam with a sperm cell and measuring the resulting light scatter or fluorescence. The determination of a sex characteristic perhaps may be made by staining the sperm cells with a fluorescent dye that binds to the DNA within individual sperm cells. When a laser illuminates individual sperm cells, the dye may fluoresce. Sorting of sperm cells according to a sex characteristic may then be accomplished, perhaps by recognizing that sperm cells bearing an X chromosome have more DNA than sperm cells bearing a Y chromosome, thus possibly emitting more fluorescent light when excited by a laser and perhaps allowing the cell to be identified and separated.

Another example of human manipulation may involve perhaps freezing sperm cells for use at a later time. Freezing sperm cells may often be critical to the effective use of sperm cells, because freezing may preserve at least some degree of the viability of sperm cells for a period of time extended beyond a point at which such viability otherwise may typically become compromised. Such extension of sperm cell viability may be accomplished in freezing techniques perhaps by slowing the metabolism of sperm cells and perhaps extending their useful life accordingly. In particular, it perhaps may be known that sperm cell metabolism may be slowed by about 50% approximately for every 10 degrees Celsius to which a sperm cell is cooled. Moreover, frozen sperm cells may be packaged in formats convenient for particular applications, for example perhaps as frozen straws, frozen pellets, or other forms of frozen artificial samples. Frozen sperm cells also may lend themselves well to transportation over large distances, for example as where a sperm cell collection facility, sperm cell extension facility, and artificial insemination facility may be widely dispersed at different locations.

It may be appreciated that the removal of sperm from their natural environment may remove them from natural support mechanisms that maintain their viability. Sperm cell extenders may act to restore at least a degree of such support to sperm cells. For example, one function of sperm cell extenders may be to buffer sperm cells, for example perhaps by adjusting the pH or osmoality of a medium into which sperm cells may be placed. Another function of sperm cells extenders perhaps may be to provide nutrients to sperm cells or to serve as a sperm cell energy source. In freezing applications, a further function may be to serve as a cryoprotectant to minimize the adverse effects of freezing upon sperm cells. It may be appreciated that such functions of sperm cell extenders may be accomplished at least to some degree by the constituent parts that make up any individual sperm cell extender.

For example, protein content may be a frequently used constituent part of various types of sperm cells extenders. Protein content may serve one or more functions in a sperm cell extender. A primary purpose of protein content may be to provide nutrients and perhaps serve as an energy source for sperm cells. However, some kinds of protein may also have a cryoprotectant function, for example, perhaps the use of lipoproteins to replace lipids lost from sperm cell membranes that may be due to a freezing process. Moreover, protein content in sperm cell extenders may take a variety of forms. Some protein content may be plant-based, for example lecithin derived from soy. Other protein content may be animal-based, for example, perhaps egg yolk derived from sources including common hen's eggs.

Cryoprotectants also may be an example of a frequently used constituent part of various types of sperm cell extenders. Moreover, cryoprotectants may take a variety of forms in sperm cell extenders. One commonly used cryoprotectant may be glycerol. Glycerol may protect sperm cells during a freezing process, perhaps by binding to water contained within and surrounding a sperm cell, perhaps dehydrating the sperm cell as a result, and accordingly perhaps reducing the formation of intracellular ice that may cause damage to the sperm cell. However, using glycerol to cryoprotect sperm cells also may entail certain disadvantages. For example, glycerol may pose at least a degree of toxicity to sperm cells, the effect of which may become more pronounced with larger amounts of glycerol. Further, glycerol may be hyperosmotic to sperm cells, which may result in a degree of shock to sperm cells to which glycerol has been added. In particular, such hyperosmotic properties of glycerol may cause a sperm cell coming into contact with glycerol to rapidly shrink or expand as a result of a difference in solute concentration across the sperm cell's membrane. Such rapid shrinking and expanding may perhaps cause damage to a sperm cell.

Accordingly, certain procedures may have been developed for sperm cell extenders to minimize the adverse effects of glycerol on sperm cells. For example, as a practical matter it may perhaps be recognized that combining glycerol with sperm cells at reduced temperatures may reduce the toxic effects of glycerol on sperm cells. Accordingly, sperm cell extenders using glycerol often may be prepared in a multiple step process involving two or more extender fractions. More particularly, certain sperm cell extenders may contain an "A" fraction without glycerol and a "B" fraction with glycerol. This may allow a sperm cell extender to be prepared in two or more steps, for example, a first step in which sperm cells may be added to the A fraction of a sperm cell extender at perhaps room temperature, followed by a second step in which the sperm cells added to the A fraction are cooled to a lower temperature, and the B fraction containing glycerol added at such a lower temperature. Moreover, to mitigate the hyperosmotic effects of glycerol on sperm cells, the B fraction perhaps may be added in multiple steps, possibly so as to reduce the shock to sperm cells by subjecting sperm cells to lowered amounts of glycerol at each added glycerol step. The number of steps in which glycerol may be added may vary from perhaps as few as two steps or four steps to perhaps a great number of steps, including perhaps adding glycerol drip-wise over a period of time.

However, the interaction of glycerol with other sperm cell extender components in such procedures may entail significant drawbacks. In particular, protein components of sperm cell extenders such as egg yolk may pose complications for the handling of such extenders when present in the B fraction. This may be due to the volumetric bulk that such protein components create in a sperm cell extender. This phenomenon perhaps may be highlighted by the use of egg yolk in the B fraction of a sperm cell extender requiring centrifugation. Centrifugation may be a commonly used technique in various sperm cell applications to concentrate sperm cells. For example, in flow cytometery applications, the passage of sperm cells through a flow cytometer may tend to dilute the concentration of sperm cells to a lower concentration than that found in nature. This may be because flow cytometers typically may require entraining sperm cells in a sheath fluid, which may add to the volume of material in which sperm cells are contained. Centrifugation may return sperm cells to a higher concentration perhaps by subjecting them to centrifugal forces and concentrating them accordingly. However, centrifuging the B fraction of a sperm cell extender containing egg yolk may be problematic because the volumetric bulk of lipoproteins contained in the egg yolk may tend to compact any sperm cells that may be present in the B fraction, perhaps with the result of crushing or otherwise damaging such sperm cells.

As a result, it may perhaps be necessary to clarify the B fraction of a sperm cell extender containing protein content such as egg yolk. The goal of clarification may be to confer a lower and more uniform degree of density to such a protein-containing extender, perhaps in particular by removing clumps or other locally dense regions due perhaps to protein concentrations such as lipoprotein components of egg yolk, so that centrifugation perhaps may be accomplished without adversely compacting sperm cells. Clarification may be accomplished by any of various suitable methods, for example perhaps by filtration. However, all forms of clarification may require a dedication of resources to accomplish. For example, clarification may entail material costs such as filters or other required devices, labor costs which may the up personnel resources that otherwise could be dedicated elsewhere, time costs which may slow down a sperm cell extension process, and financial costs related to all of the foregoing.

Moreover, simply preparing a B fraction of a sperm cell extender to contain protein content such as egg yolk may entail a degree of inherent drawbacks. Similarly to clarification, preparation of such a B fraction may entail material costs, labor costs, time costs, and financial costs. Moreover, the tendency toward spoliation over time due to the protein content of such a B fraction may further complicate its use. In particular, because such a B fraction may not keep well, it may require preparation on an as-needed basis, perhaps disrupting schedules and reducing efficiencies that could be realized if the B fraction otherwise could be prepared in large quantities ahead of time. This drawback may be particularly acute in situations where a sperm cell application may require a relatively high ratio of B fraction to A fraction. The spoliation tendencies of such a B fraction may also pose a contamination risk, for example as where the B fraction may perhaps become contaminated with bacteria due to spoliation, which may adversely affect a sperm cell application in which the contaminated B fraction inadvertently may be used. Such spoliation tendencies also may limit the use of such a B fraction in situations where environmental conditions cannot be closely monitored, for example as where it may be desired to transport the B fraction from one location to another perhaps over a large distance.

The foregoing problems regarding conventional sperm cell extenders may represent a long-felt need for an effective solution to the same. While implementing elements may have been available, actual attempts to meet this need may have been lacking to some degree. This may have been due to a failure of those having ordinary skill in the art to fully appreciate or understand the nature of the problems and challenges involved. As a result of this lack of understanding, attempts to meet these long-felt needs may have failed to effectively solve one or more of the problems or challenges here identified. These attempts may even have led away from the technical directions taken by the present inventive technology and may even result in the achievements of the present inventive technology being considered to some degree an unexpected result of the approach taken by some in the field.

SUMMARY OF THE INVENTION

The inventive technology relates to methods and apparatus for reducing protein content in sperm cell extenders and may include one or more of the following features: techniques for reducing protein content in a sperm cell extender; techniques for reducing protein content in a cryoprotectant-containing B fraction of a sperm cell extender; techniques for preparing sperm cell extenders that do not require clarification; techniques for preparing low density gradient sperm cell extenders suitable for centrifugation; techniques for reducing protein content between individual steps in preparing a sperm cell extender, and techniques for establishing novel values of reduced protein content in sperm cell extenders. Accordingly, the objects of the methods and apparatus for reducing protein content in sperm cell extenders described herein address each of the foregoing problems in a practical manner. Naturally, further objects of the invention will become apparent from the description and drawings below.

DETAILED DESCRIPTION OF THE PREFERRED EMBODIMENTS

The present inventive technology includes a variety of aspects, which may be combined in different ways. The following descriptions are provided to list elements and describe some of the embodiments of the present inventive technology. These elements are listed with initial embodiments, however it should be understood that they may be combined in any manner and in any number to create additional embodiments. The variously described examples and preferred embodiments should not be construed to limit the present inventive technology to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 1:
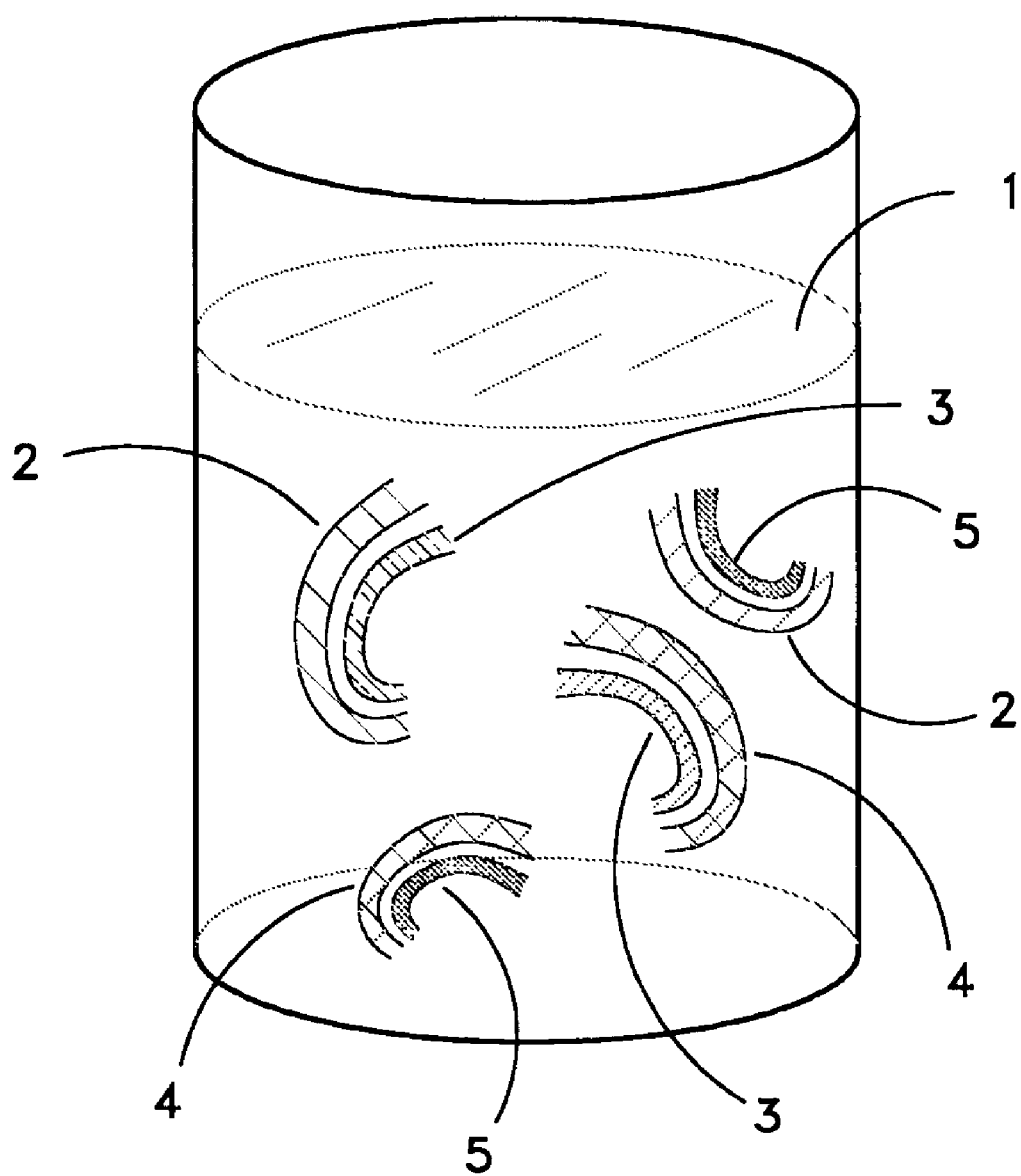
FIG. 1 is a depiction of various nascent substances in admixture relation.

Now referring primarily to FIG. 1, some embodiments may include a method for freezing sorted sperm cells compromised by a sorting event. The term sorting event may be understood to include any of a variety of events in which sperm cells are sorted based on a discrimination of characteristics retained by such sperm cells, which may include in various embodiments immunosexing techniques, buoyancy techniques, or perhaps even flow cytometery techniques. The term compromised may be understood to include any effect of a sorting event that may tend to adversely affect any desired aspect for which the sperm cells may be used, including for example sperm cell viability, sperm cell fecundity, or perhaps even sperm cell longevity. The term freezing may be understood to include any technique for preserving sperm cells that includes depressing their temperature below 0 degrees Celsius at least at some point in the technique.

Moreover, embodiments may involve obtaining a plurality of sperm cells, subjecting such a plurality of sperm cells to sorting stresses, and selecting such a plurality of sperm cells for a desired characteristic. By the term obtaining, it may be understood that any of various known techniques for obtaining sperm cells may be used, for example perhaps including manual techniques or techniques involving an artificial vagina. The term sorting stresses may be understood to include stresses that sperm cells may experience as a result of a sorting event, and subjecting sperm cells to sorting stresses may include perhaps merely accomplishing a sorting event.

A protein-containing sperm cell extender may be added to a plurality of selected sperm cells in some embodiments to form a first extended sperm cell mixture. The term sperm cell extender may be understood to include a substance that confers at least some degree of maintenance function to sperm cells. Such kinds of maintenance function may include, for example, serving to buffer sperm cells, providing nutrients to sperm cells, or perhaps even acting as a cryoprotectant for sperm cells. It may be appreciated that various kinds of sperm cell extenders may be known, perhaps including egg yolk based extenders, milk based extenders, citrate containing extenders, sodium-citrate containing extenders, Tris containing extenders, and TEST containing extenders. Moreover, the term first extended sperm cell mixture may be understood to include the combination of such a protein-containing sperm cell extender with such a plurality of selected sperm cells.

Various embodiments may further involve cooling such a first extended sperm cell mixture to create a first cooled extended sperm cell mixture. The term cooling may be understood to include reducing the temperature of a first extended sperm cell mixture to any temperature above 0 degrees Celsius. Cooling may perhaps be accomplished by any of various well-known techniques, such as perhaps refrigeration, water baths, or ice baths. In various embodiments, a first extended sperm cell mixture may be cooled perhaps to less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. Certain embodiments may involve cooling a first extended sperm cell mixture to about 5 degrees Celsius. Moreover, a protein-free cryoprotectant-containing sperm cell extender may be added to such a first cooled extended sperm cell mixture in some embodiments to form a second cooled extended sperm cell mixture. The term second cooled extended sperm cell mixture may be understood to include the combination of such a first cooled extended sperm cell mixture with such a protein-free cryoprotectant-containing sperm cell extender. Various embodiments may also include freezing such a second cooled extended sperm cell mixture.

A first extended sperm cell mixture in some embodiments may contain a percentage of egg yolk. This may be a function, for example, of the amount of protein contained within a protein-containing sperm cell extender added to a plurality of selected sperm cells, wherein such a protein may be egg yolk. In various embodiments, the percentage of egg yolk contained within a first extended sperm cell mixture may include more than about 0.8 percent egg yolk, more than about 1.6 percent egg yolk, more than about 3.2 percent egg yolk, or perhaps even more than about 6.4 percent egg yolk. Some embodiments may include a percentage of egg yolk contained within a first extended sperm cell mixture of about 3.2 percent.

Moreover, a second cooled extended sperm cell mixture in some embodiments also may contain a percentage of egg yolk. This may be a function, for example, of perhaps a dilution effect of adding a protein-free cryoprotectant-containing sperm cell extender to a first cooled extended sperm cell mixture. In various embodiments, the percentage of egg yolk contained within a second cooled extended sperm cell mixture may include more than about 0.4 percent egg yolk, more than about 0.8 percent egg yolk, more than about 1.6 percent egg yolk, or perhaps even more than about 3.2 percent egg yolk. Some embodiments may include a percentage of egg yolk contained with a second cooled extended sperm cell mixture of about 1.6 percent.

In some embodiments, a second cooled extended sperm cell mixture may be maintained in an unclarified state. In maintaining a second cooled extended sperm cell mixture in an unclarified state, it may be understood that such a second cooled extended sperm cell mixture may not be subject to clarification prior to any step of centrifuging. Moreover, certain embodiments may involve subjecting such a second cooled extended sperm cell mixture to centrifugation. This centrifugation may perhaps serve to concentrate sperm cells contained within such a second cooled extended sperm cell mixture, perhaps by separating such sperm cells from other components of the second cooled extended sperm cell mixture on a density basis due to the application of centrifugal force to the sperm cells. Various embodiments may further involve decanting a portion of such a centrifuged second cooled extended sperm cell mixture. For example, sperm cells concentrated by centrifugation may be concentrated largely within one area, and removing a volumetric section perhaps may include removing the volumetric section containing such concentrated sperm cells or perhaps even removing all volumetric sections not including such concentrated sperm cells.

Figure 2A:
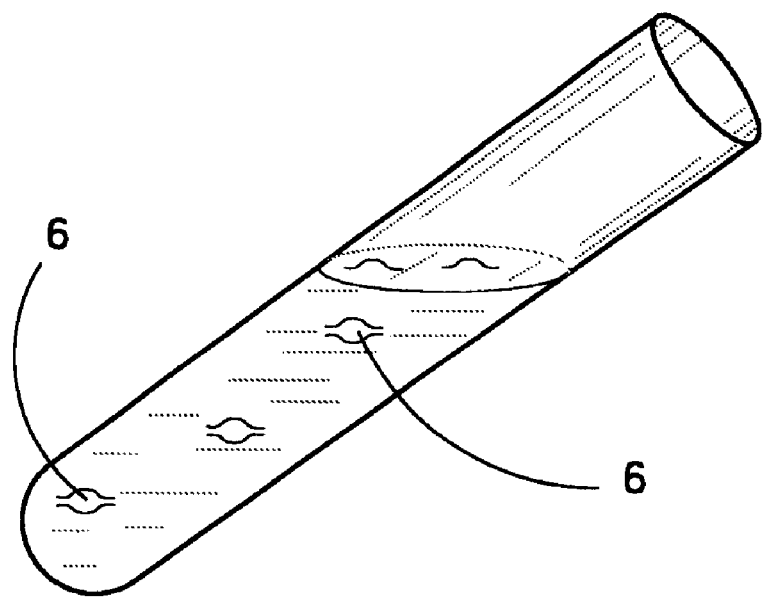
FIG. 2a is a depiction of a prior art sperm cell extender.
Figure 2B:
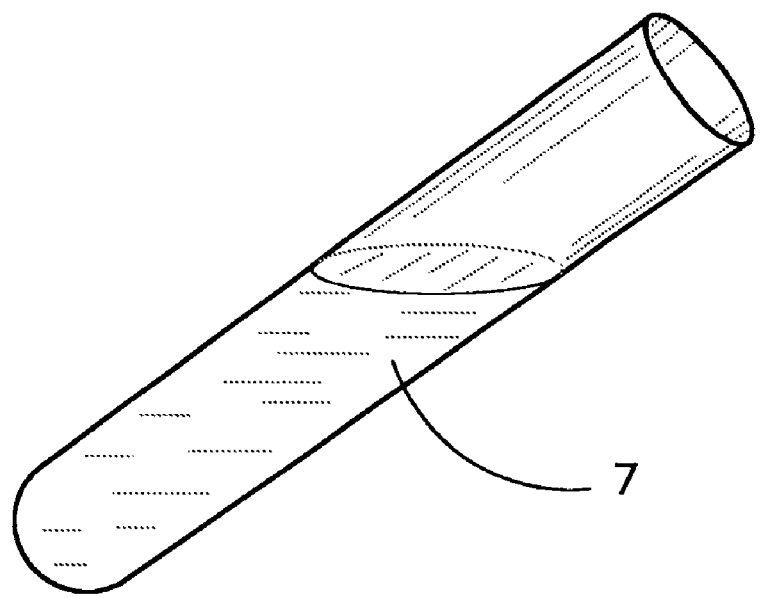
FIG. 2b is a depiction of an unclarified centrifugation medium.

Now referring primarily to FIG. 2, some embodiments may include a method for processing sorted sperm cells compromised by a sorting event. The term processing may be understood to include any event in which sperm cells are treated to change at least one characteristic of such sperm cells by at least some degree. In various embodiments, processing may include for example freezing, thawing, or perhaps even centrifuging such sperm cells.

Moreover, embodiments may involve obtaining a plurality of sperm cells, subjecting such a plurality of sperm cells to sorting stresses, and selecting such a plurality of sperm cells for a desired characteristic. Some embodiments further may include providing a protein-free sperm cell extender, providing a protein-free cryoprotectant-containing sperm cell extender, and combining such a protein-free sperm cell extender with such a protein-free cryoprotectant-containing sperm cell extender to form a cryoprotectant-containing centrifugation medium. The term centrifugation medium may be understood to include any medium conducive to sperm cells that at some point is subjected to centrifugation.

In some embodiments, combining such a protein-free sperm cell extender with such a protein-free cryoprotectant-containing sperm cell extender to form a cryoprotectant-containing centrifugation medium may be accomplished at a cool temperature. Such a cool temperature may include less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. Certain embodiments may involve combining such a protein-free sperm cell extender with such a protein-free cryoprotectant-containing sperm cell extender to form a cryoprotectant-containing centrifugation medium at about 5 degrees Celsius.

A cryoprotectant-containing centrifugation medium in some embodiments may be maintained in an unclarified state. An unclarified state may be understood to include a state in which a substance may exist wherein such a substance has not been clarified. Clarification may be understood to include conferring a lower and more uniform degree of density to a substance, and perhaps may involve techniques such as filtering or straining. In maintaining a cryoprotectant-containing centrifugation medium in an unclarified state, it may be understood that such a cryoprotectant-containing centrifugation medium may not be subject to clarification prior to any step of centrifuging.

Various embodiments may further involve adding a plurality of sperm cells subjected to sorting stresses and selected for a desired characteristic to such an unclarified cryoprotectant-containing centrifugation medium, perhaps to form an unclarified cryoprotectant-containing sperm cell centrifugation medium. The term unclarified cryoprotectant-containing sperm cell centrifugation medium may be understood to include perhaps simply an unclarified cryoprotectant-containing centrifugation medium to which such a plurality of sperm cells has been added. Moreover, certain embodiments may involve subjecting such an unclarified cryoprotectant-containing sperm cell centrifugation medium to centrifugation. The term centrifugation may be understood to include applying a centrifugal force to a substance in order to separate at least two constituent components of that substance based on density. This centrifugation may perhaps serve to concentrate sperm cells contained within such an unclarified cryoprotectant-containing sperm cell centrifugation medium, perhaps by separating such sperm cells from other components of the unclarified cryoprotectant-containing sperm cell centrifugation medium on a density basis due to the application of centrifugal force to the sperm cells.

Various embodiments may further involve decanting a portion of such a centrifuged unclarified cryoprotectant-containing sperm cell centrifugation medium. Decanting may be understood to include removing at least some volumetric section of a substance, perhaps such a centrifuged unclarified cryoprotectant-containing sperm cell centrifugation medium, which perhaps may be achieved by any of various well-known techniques, including for example pouring off such a volumetric section. Significantly, it may be possible to select such a volumetric section to be removed based on the amount of a centrifuged component present in such a volumetric section. For example, sperm cells concentrated by centrifugation may be concentrated largely within one area, and removing a volumetric section perhaps may include removing the volumetric section containing such concentrated sperm cells or perhaps even removing all volumetric sections not including such concentrated sperm cells.

Certain embodiments may further involve providing a protein-containing sperm cell extender and combining such a protein-containing sperm cell extender with a cryoprotectant-containing centrifugation medium to create a protein-containing cryoprotectant-containing centrifugation medium. Moreover, various embodiments may further include adding a plurality of sperm cells subjected to sorting stresses and selected for a desired characteristic to such a protein-containing cryoprotectant-containing centrifugation medium to create a protein-containing cryoprotectant-containing sperm cell centrifugation medium. Some embodiments may further involve maintaining such a protein-containing cryoprotectant-containing sperm cell centrifugation medium in an unclarified state.

Moreover, such a protein-containing cyroprotectant-containing sperm cell centrifugation medium in certain embodiments may contain a percentage of egg yolk. This may be a function, for example, of the amount of protein contained with a protein-containing sperm cell extender combined with a cryoprotectant-containing centrifugation medium, wherein such a protein may be egg yolk. In various embodiments, the percentage of egg yolk contained within a protein-containing cyroprotectant-containing sperm cell centrifugation medium may include more than about 0.4 percent egg yolk, more than about 0.8 percent egg yolk, more than about 1.6 percent egg yolk, or perhaps even more than about 3.2 percent egg yolk. Some embodiments may include a percentage of egg yolk contained within a protein-containing cyroprotectant-containing sperm cell centrifugation medium of about 1.6 percent.

In some embodiments, subjecting a protein-containing cyroprotectant-containing sperm cell centrifugation medium to centrifugation perhaps may include centrifuging such a protein-containing cyroprotectant-containing sperm cell centrifugation medium having a fraction of the percentage of egg yolk as compared to a centrifugation medium utilized in a typical method for centrifuging sorted sperm cells. Typical methods for centrifuging sorted sperm cells may be understood to include perhaps all methods for centrifuging sorted sperm cells not utilizing the novel techniques disclosed herein, and particularly may include perhaps those methods for centrifuging sorted sperm cells that may be well known in the art. Moreover, the term fraction may be understood to include an amount of egg yolk less than that contained in a centrifugation medium utilized in such a typical method. In some embodiments, such a fraction may include perhaps less than about 50 percent as compared to a centrifugation medium utilized in a typical method for centrifuging sorted sperm cells, less than about 25 percent as compared to a centrifugation medium utilized in a typical method for centrifuging sorted sperm cells, less than about 10 percent as compared to a centrifugation medium utilized in a typical method for centrifuging sorted sperm cells, less than about 5 percent as compared to a centrifugation medium utilized in a typical method for centrifuging sorted sperm cells, less than about 4 percent as compared to a centrifugation medium utilized in a typical method for centrifuging sorted sperm cells, less than about 3 percent as compared to a centrifugation medium utilized in a typical method for centrifuging sorted sperm cells, less than about 2 percent as compared to a centrifugation medium utilized in a typical method for centrifuging sorted sperm cells, or perhaps even less than about 1 percent as compared to a centrifugation medium utilized in a typical method for centrifuging sorted sperm cells. In some embodiments, such a fraction of the percentage of egg yolk as compared to a centrifugation medium utilized in a typical method for centrifuging sorted sperm cells may be a protein-containing cryoprotectant-containing sperm cell centrifugation medium having less than about 3 percent egg yolk. Some embodiments perhaps may even include centrifuging a protein-containing cryoprotectant-containing sperm cell centrifugation medium containing glycerol and having less than about 11 percent egg yolk.

Figure 3:
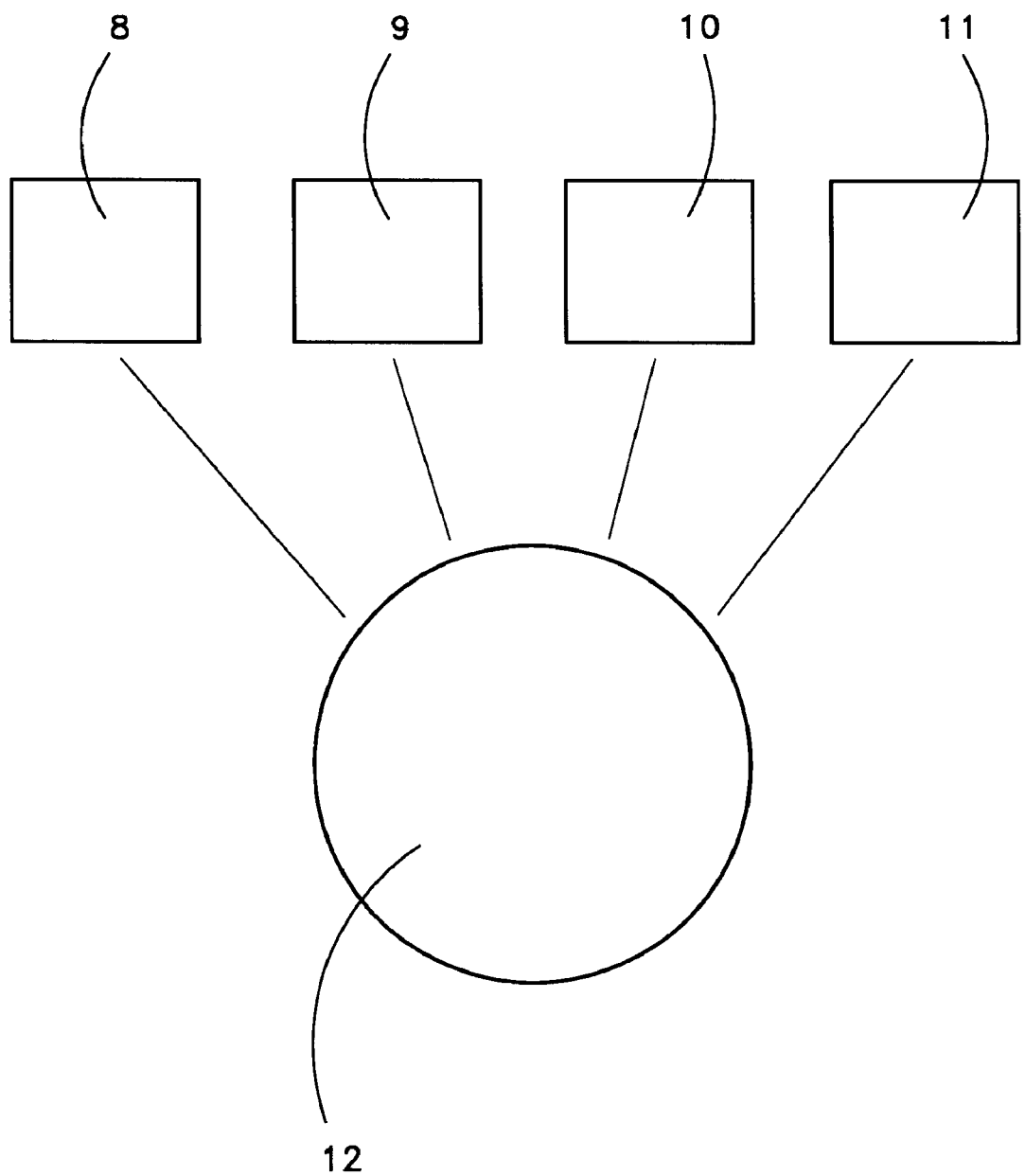
FIG. 3 is a representation of an intermediate sperm cell extender.

Now referring primarily to FIG. 3, some embodiments may involve a method for extending sorted sperm cells compromised by a sorting event. The term extending may be understood to include conferring to sperm cells at least one or more of the functionalities of a sperm cell extender.

Moreover, various embodiments may include obtaining a plurality of sperm cells, subjecting such a plurality of sperm cells to sorting stresses, and selecting such a plurality of sperm cells for a desired characteristic. Embodiments may further include establishing a protein-containing sperm cell extender having a first protein content value. Such a first protein-content value may be understood to include the protein content of such an established protein-containing sperm cell extender prior to any subsequent events that may alter such a protein content.

Various embodiments may also include adding a plurality of sperm cells subjected to sorting stresses and selected for a desired characteristic to a protein-containing sperm cell extender having a first protein content value and also adding a protein-free sperm cell extender, perhaps including a protein-free cryoprotectant-containing sperm cell extender, to said protein-containing sperm cell extender having a first protein content value. In various embodiments, adding a protein-free cyroprotectant-containing sperm cell extender to a protein-containing sperm cell extender having a first protein content value may be accomplished at a cool temperature. Such a cool temperature may include less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. Certain embodiments may involve adding a protein-free sperm cell extender to a protein-containing sperm cell extender having a first protein content value at about 5 degrees Celsius.

Moreover, some embodiments may further include reducing a total protein content of such a protein-containing sperm cell extender having a first protein content value to a second protein content value below such a first protein content value. A total protein content perhaps simply may be the total amount of protein in a protein-containing sperm cell extender at any given time, and the term reducing a total protein content may be understood to include any of various suitable methods for accomplishing such a reduction, including perhaps directly removing protein content or perhaps simply increasing the amount of non-protein components in such a protein-containing sperm cell extender.

A first protein content value in some embodiments may include a percentage of egg yolk, for example, wherein such a protein may be egg yolk. In various embodiments, such a percentage of egg yolk may include more than about 0.8 percent egg yolk, more than about 1.6 percent egg yolk, more than about 3.2 percent egg yolk, or perhaps even more than about 6.4 percent egg yolk. Some embodiments may include a percentage of egg yolk of about 3.2 percent.

Moreover, reducing a total protein content to a second protein content value below such a first protein content value in some embodiments may include reducing a percentage of egg yolk of such a protein-containing sperm cell extender. This may be a function, for example, of perhaps a dilution effect of adding a plurality of sperm cells and adding a protein-free sperm cell extender to such a protein-containing sperm cell extender. In various embodiments, such a percentage of egg yolk of a second protein content value may include more than about 0.4 percent egg yolk, more than about 0.8 percent egg yolk, more than about 1.6 percent egg yolk, or perhaps even more than about 3.2 percent egg yolk. In some embodiments such a percentage of egg yolk of a second protein content value may be about 1.6 percent.

In some embodiments, such a protein-containing sperm cell extender having a second protein content value may be maintained in an unclarified state. In maintaining a protein-containing sperm cell extender having a second protein content value in an unclarified state, it may be understood that such a protein-containing sperm cell extender having a second protein content value may not be subject to clarification prior to any step of centrifuging. Moreover, certain embodiments may involve subjecting such a protein-containing sperm cell extender having a second protein content value to centrifugation. This centrifugation may perhaps serve to concentrate sperm cells contained within such a protein-containing sperm cell extender having a second protein content value, perhaps by separating such sperm cells from other components of a protein-containing sperm cell extender having a second protein content value on a density basis due to the application of centrifugal force to the sperm cells. Various embodiments may further involve decanting a portion of such a centrifuged protein-containing sperm cell extender having a second protein content value. For example, sperm cells concentrated by centrifugation may be concentrated largely within one area, and removing a volumetric section perhaps may include removing the volumetric section containing such concentrated sperm cells or perhaps even removing all volumetric sections not including such concentrated sperm cells.

Various embodiments may also include adding a supplemental protein-containing sperm cell extender to a protein-containing sperm cell extender having a second protein content value and increasing a total protein content of such a protein-containing sperm cell extender to a third protein content value higher than a first protein content value. The term supplemental protein-containing sperm cell extender may be understood to include any additional protein-containing sperm cell extender that supplements a protein-containing sperm cell extender having a second protein content value. The term supplement may be understood to include adding additional sperm cell extender components, for example perhaps adding an additional amount of protein.

Further, increasing a total protein content to a third protein content value in some embodiments may include increasing a percentage of egg yolk of such a protein-containing sperm cell extender. This may be a function, for example, of perhaps adding a supplemental protein-containing sperm cell extender to a protein-containing sperm cell extender having a second protein content value. In various embodiments, such a percentage of egg yolk of a third protein content value may include more than about 1 percent egg yolk, more than about 5 percent egg yolk, more than about 10 percent egg yolk, more than about 15 percent egg yolk, more than about 20 percent egg yolk, more than about 25 percent egg yolk, or perhaps even more than about 50 percent egg yolk. In some embodiments such a percentage of egg yolk of a third protein content value may be about 16.5 percent. Moreover, various embodiments may include freezing a protein-containing sperm cell extender having a third protein content value higher than a first protein content value.

Now referring to FIGS. 1-3, in various embodiments a plurality of sperm cells may include perhaps a plurality of mammalian sperm cells, including for example perhaps a plurality of bovine sperm cells, a plurality of equine sperm cells, a plurality of porcine sperm cells, a plurality of ovine sperm cells, a plurality of cervid sperm cells, a plurality of canine sperm cells, or perhaps even a plurality of delphinidae sperm cells. Moreover, some embodiments may involve selecting such a plurality of sperm cells for a desired characteristic. The term selecting may be understood to include identifying individual sperm cells based on a determination as to whether or not they possess a desired characteristic being sought. In some embodiments, selecting sperm cells for a desired characteristic may include sorting sperm cells. The term sorting may be understood to include acting to separate selected sperm cells having a desired characteristic from those sperm cells not having such a desired characteristic, perhaps including into populations of sperm cells with such a desired characteristic and populations of sperm cells without such a desired characteristic. Sorting sperm cells may be accomplished by any of a variety of suitable techniques, including perhaps immunosexing techniques, buoyancy techniques, or perhaps even flow cytometery techniques. Additionally, the term desired characteristic may be understood to include any identifiable characteristic of a sperm cell desired for a given sperm cell application. For example, in some embodiments a desired characteristic may include a sex characteristic of a sperm cell, perhaps even an X-chromosome-bearing characteristic of a sperm cell or a Y-chromosome-bearing characteristic of a sperm cell.

The term protein-containing sperm cell extender in various embodiments may be understood to include any sperm cell extender containing at least some degree of protein content. Moreover, in various embodiments a protein-containing sperm cell extender may include perhaps plant-based protein content or perhaps animal-based protein content, which may be understood to include proteins derived from plant sources and animal sources respectively. In certain embodiments, an animal-based protein-containing sperm cell extender perhaps may include a lipoprotein-containing sperm cell extender. It may be appreciated that lipoproteins may be perhaps a subclass of proteins in which at least one component of such a protein is a lipid. Such a lipoprotein content may perhaps be derived from various animal sources, including perhaps egg yolk collected from various kinds of animal eggs, perhaps including hen's eggs.

Accordingly, in certain embodiments a protein-containing sperm cell extender perhaps may include an egg-yolk-containing sperm cell extender. It may be appreciated that the precise egg yolk content of such an egg-yolk-containing sperm cell extender may be varied depending on the needs of a particular application for which sperm cells may be used. However, in some embodiments an egg yolk content of an egg-yolk-containing sperm cell extender may include less than about 50 percent egg yolk, less than about 45 percent egg yolk, less than about 40 percent egg yolk, less than about 35 percent egg yolk, less than about 30 percent egg yolk, less than about 25 percent egg yolk, less than about 20 percent egg yolk, less than about 15 percent egg yolk, less than about 10 percent egg yolk, or perhaps even less than about 5 percent egg yolk. In certain embodiments, an egg yolk content of an egg-yolk-containing sperm cell extender may be about 20 percent egg yolk.

A cryoprotectant may be included as a constituent part of a sperm cell extender in various embodiments. Accordingly, a sperm cell extender in various embodiments may include perhaps a protein-free cryoprotectant-containing sperm cell extender or perhaps even a protein-containing cyroprotectant-containing sperm cell extender. It may be appreciated that various well-known cryoprotectants perhaps may be appropriate for such addition to a sperm cell extender. In various embodiments, such a cryoprotectant perhaps may include glycerol. It may be appreciated that the precise glycerol content of such a glycerol-containing sperm cell extender may be varied depending on the needs of a particular application for which sperm cells may be used. However, in some embodiments a glycerol-containing sperm cell extender may have more than about 3 percent glycerol, more than about 6 percent glycerol, more than about 12 percent glycerol, or perhaps even more than about 24 percent glycerol. In certain embodiments, a glycerol content of a glycerol-containing sperm cell extender may be about 6 percent.

Moreover, in certain embodiments a protein-free cryoprotectant-containing sperm cell extender may be added to a substance in an equal volume to that substance, perhaps including accomplishing such an addition in multiple steps. For example, adding a protein-free cryoprotectant-containing sperm cell extender to a first cooled extended sperm cell mixture may involve adding such a protein-free cryoprotectant-containing sperm cell extender having a volume equal to a volume of such a first cooled extended sperm cell mixture, perhaps in two or more steps. Similarly, combining a protein-free cryoprotectant-containing sperm cell extender and a protein-free sperm cell extender may involve adding such a protein-free cryoprotectant-containing sperm cell extender in a volume equal to a volume of such a protein-free sperm cell extender, perhaps in two or more steps. Further, adding a protein-free cryoprotectant-containing sperm cell extender to a protein-containing sperm cell extender may involve adding such a protein-free cryoprotectant-containing sperm cell extender having a volume equal to a volume of such a protein-containing sperm cell extender, perhaps in two or more steps.

A protein-free cryoprotectant-containing sperm cell extender in certain embodiments may include a low density gradient cryoprotectant-containing sperm cell extender. Accordingly, in some embodiments adding a protein-free cryoprotectant-containing sperm cell extender to a first cooled extended sperm cell mixture may involve adding a low density gradient cryoprotectant-containing sperm cell extender to such a first cooled extended sperm cell mixture. Further, in some embodiments providing a protein-free cryoprotectant-containing sperm cell extender may involve providing a low density gradient cryoprotectant-containing sperm cell extender. Also, in some embodiments adding a protein-free cryoprotectant-containing sperm cell extender to a protein-containing sperm cell extender may involve adding a low density gradient cryoprotectant-containing sperm cell extender to such a protein-containing sperm cell extender.

The term low density gradient may be understood to include a sperm cell extender having minimal density variations throughout its volume. In some embodiments, a low density gradient cryoprotectant-containing sperm cell extender may perhaps include a substantially liquid cryoprotectant-containing sperm cell extender. The term substantially liquid may be understood to include a cryoprotectant-containing sperm cell extender wherein all constituent parts of such a cryoprotectant-containing sperm cell extender are in a substantially liquid state. In various embodiments, a low density gradient cryoprotectant-containing sperm cell extender may perhaps include a centrifugation-efficient cryoprotectant-containing sperm cell extender. The term centrifugation-efficient may be understood to include a cryoprotectant-containing sperm cell extender having properties conducive to centrifugation, for example perhaps including clearly demarcated density differences in its constituent parts or perhaps even a lack of localized higher density regions that may pose a compaction risk to certain of its constituent parts. In various embodiments, a low density gradient cryoprotectant-containing sperm cell extender may perhaps include a substantially uniform density cryoprotectant-containing sperm cell extender, which may be understood to include a minimal number of localized areas of higher density, perhaps even approaching no areas of localized higher density. In various embodiments, a low density gradient cryoprotectant-containing sperm cell extender may perhaps include a cryoprotectant-containing sperm cell extender with substantially no sperm cell compaction particles. The term sperm cell compaction particle may be understood to include any particle or group of particles joined together that may tend to compact sperm cells to a damaging degree when subjected to various types of forces, perhaps including centrifugal forces. In various embodiments, a low density gradient cryoprotectant-containing sperm cell extender may perhaps include a low viscosity cryoprotectant-containing sperm cell extender. The term low viscosity may be understood to include a viscosity of a cryoprotectant-containing sperm cell extender sufficient to permit its constituent parts to slip past each other without tending toward the compaction of any one constituent part by any other constituent part.

Various embodiments may include adjusting a sperm cell concentration of a substance to a pre-freeze sperm cell concentration. The term pre-freeze sperm cell concentration may be understood to include a concentration of sperm cells at which such sperm cells may subsequently be frozen. For example, some embodiments may involve adjusting a sperm cell concentration of a second cooled extended sperm cell mixture to a pre-freeze sperm cell concentration, while other embodiments may involve adjusting a sperm cell concentration of a protein-containing sperm cell extender having a second protein content value to a pre-freeze sperm cell concentration. In various embodiments, adjusting to such a pre-freeze sperm cell concentration may include adding a protein-containing sperm cell extender, including for example perhaps adding a protein-containing sperm cell extender to a second extended sperm cell mixture or perhaps adding a supplemental protein-containing sperm cell extender to a protein-containing sperm cell extender having a second protein content value.

In various embodiments, adjusting a sperm cell concentration to a pre-freeze sperm cell concentration may involve adjusting a sperm cell concentration to a species-appropriate pre-freeze concentration. The term species-appropriate pre-freeze sperm cell concentration my be understood to include a concentration of sperm cells at which such sperm cells may subsequently be frozen that is appropriate for the species of animal from which such sperm cells were obtained. It may be appreciated that a species-appropriate pre-freeze sperm cell concentration may be known for a variety of animal species, or perhaps even may determined through routine empirical observation over a number of freezing events. In some embodiments, a species-appropriate pre-freeze sperm cell concentration may include a bovine pre-freeze sperm cell concentration, an equine pre-freeze sperm cell concentration, a porcine pre-freeze sperm cell concentration, an ovine pre-freeze sperm cell concentration, a cervid pre-freeze sperm cell concentration, a canine pre-freeze sperm cell concentration, or perhaps even a delphinidae sperm cell concentration. Moreover, in various embodiments a species-appropriate pre-freeze sperm cell concentration may include less than about 100 million sperm cells per milliliter, less than about 50 million sperm cells per milliliter, less than about 40 million sperm cells per milliliter, less than about 30 million sperm cells per milliliter, less than about 20 million sperm cells per milliliter, less than about 15 million sperm cells per milliliter, less than about 10 million sperm cells per milliliter, less than about 5 million sperm cells per milliliter, or perhaps even less than about 2 million sperm cells per milliliter. In certain embodiments, perhaps including those involving a bovine pre-freeze sperm cell concentration, a species-appropriate pre-freeze concentration may be about 10 million sperm cells per milliliter.

Adjusting a sperm cell concentration to a pre-freeze sperm cell concentration in some embodiments may include establishing a pre-freeze egg yolk content. For example, adjusting a sperm cell concentration of a second cooled extended sperm cell mixture to a pre-freeze sperm cell concentration may include establishing a pre-freeze egg yolk content of such second extended sperm cell mixture. Similarly, adjusting a sperm cell concentration of a protein-containing sperm cell extender having a second protein content value to a pre-freeze sperm cell concentration may include establishing a pre-freeze egg yolk content of such a protein-containing sperm cell extender. A pre-freeze egg yolk content may be understood to include perhaps simply an egg yolk content of a substance at a pre-freeze concentration. In various embodiments, a pre-freeze egg yolk content may include an egg yolk content within a percentage of the egg yolk content of a typical method for freezing sorted sperm cells. Such a typical method for freezing sorted sperm cells may be understood to include perhaps all methods for freezing sorted sperm cells not utilizing the novel techniques disclosed herein, and particularly may include perhaps those methods for freezing sorted sperm cells that may be well known in the art. In various embodiments, a pre-freeze egg yolk content may include may include perhaps within about 50 percent of the pre-freeze egg yolk content of a typical method for freezing sorted sperm cells, within about 25 percent of the pre-freeze egg yolk content of a typical method for freezing sorted sperm cells, within about 20 percent of the pre-freeze egg yolk content of a typical method for freezing sorted sperm cells, within about 15 percent of the pre-freeze egg yolk content of a typical method for freezing sorted sperm cells, within about 10 percent of the pre-freeze egg yolk content of a typical method for freezing sorted sperm cells, within about 5 percent of the pre-freeze egg yolk content of a typical method for freezing sorted sperm cells, within about 2 percent of the pre-freeze egg yolk content of a typical method for freezing sorted sperm cells, and perhaps even within about 1 percent of the pre-freeze egg yolk content of a typical method for freezing sorted sperm cells.

Moreover, in certain embodiments a pre-freeze egg yolk content perhaps may be established at an absolute value of less than about 50 percent egg yolk, less than about 45 percent egg yolk, less than about 40 percent egg yolk, less than about 35 percent egg yolk, less than about 30 percent egg yolk, less than about 25 percent egg yolk, less than about 20 percent egg yolk, less than about 15 percent egg yolk, or perhaps even less than about 10 percent egg yolk. In some embodiments, a pre-freeze egg yolk content may be established at about 16.5 percent.

The use of a sterile sperm cell extender may be involved in certain embodiments. For example, in various embodiments a protein-free sperm cell extender may include a sterile protein-free sperm cell extender, and a protein-free cryoprotectant-containing sperm cell extender may include a sterile protein-free cryoprotectant-containing sperm cell extender.

Now with further reference primarily to FIG. 1, various embodiments may include an incipient admixture (1), which in various embodiments perhaps may include an incipient compromised sorted sperm cell admixture. An admixture may be understood to include two or more substances in a state of being mixed, and an incipient admixture (1) may be understood to include an admixture that is less than completely saturated with respect to any two constituent components capable of being mixed. In various embodiments, an incipient admixture (1) may include perhaps an admixture that has achieved less than 50 percent saturation, less than 25 percent saturation, less than 10 percent saturation, less than 5 percent saturation, less than 2 percent saturation, or perhaps even less than 1 percent saturation.

Some embodiments may include two or more nascent substances in incipient admixture relation. An incipient admixture relation may be understood to include two or more substances related by existing together in an incipient admixture (1). A nascent substance may be understood to include a substance that exists in a less than saturated combination with another substance in incipient admixture relation. Moreover, an admixture in some embodiments may include two or more nascent components, wherein such a component may be understood to be a component of an incipient admixture (1). For example, various embodiments may include a nascent plurality of sperm cells selected for a desired characteristic (2) in incipient admixture relation, a nascent protein-free sperm cell extender component in incipient admixture relation (3), a nascent protein-free cryoprotectant-containing sperm cell extender component in incipient admixture relation (4), or perhaps even a nascent protein-containing sperm cell extender component in incipient admixture relation (5).

In some embodiments, a nascent substance may include a substance proximately located in a substantially uncombined state to at least one component of an incipient admixture (1). The term proximately located may be understood to include a location of such a nascent substance near enough to such a component of an incipient admixture (1) so as to permit a combination of the two. The term substantially uncombined state may be understood to include the existence of such a nascent substance in a state of mostly unsaturated combination with such a component of an incipient admixture (1), which may include perhaps existing as more than 50 percent uncombined, existing as more than 75 percent uncombined, existing as more than 90 percent uncombined, existing as more than 95 percent uncombined, or perhaps even existing as more than 99 percent uncombined. For example, various embodiments may include a plurality of sperm cells selected for a desired characteristic proximately located in a substantially uncombined state to at least one component of an incipient admixture (1), a protein-free sperm cell extender component proximately located in a substantially uncombined state to at least one component of an incipient admixture (1), a protein-free cryoprotectant-containing sperm cell extender component proximately located in a substantially uncombined state to at least one component of an incipient admixture (1), or perhaps even a protein-containing sperm cell extender component proximately located in a substantially uncombined state to at least one component of an incipient admixture (1).

Moreover, certain embodiments may include a barrier-free zone between a nascent substance and a component of an incipient admixture (1). Such a barrier free zone may be understood to include a zone containing no elements that may tend to prevent the combination of such a nascent substance and such a component of an incipient admixture (1). Some embodiments may even involve an induced combination force to which a nascent substance and a component of an incipient admixture (1) may be responsive. Such an induced combination force may be understood to include any force tending to induce a combination of two or more substances in incipient admixture relation. Examples of an induced combination force may include perhaps a density-related force, a concentration-related force, or perhaps even simple hydrodynamic forces generated by placing various liquids in a container. The term responsive may be understood to include any effect on such a nascent substance or component of an incipient admixture (1) caused by such an induced combination force.

Moreover, an incipient admixture (1) in some embodiments may contain an egg yolk content. This may be a function, for example, of the amount of protein in a nascent protein-containing sperm cell extender component, perhaps wherein such protein may be egg yolk. In various embodiments, the percentage of egg yolk contained within an incipient admixture may include more than about 0.4 percent egg yolk, more than about 0.8 percent egg yolk, more than about 1.6 percent egg yolk, or perhaps even more than about 3.2 percent egg yolk. Some embodiments may include a percentage of egg yolk contained with an incipient admixture (1) of about 1.6 percent.

In various embodiments, an incipient admixture (1) may include an unclarified incipient admixture (1). Various embodiments also may include a cool incipient admixture. In some embodiments, a cool incipient admixture may be an incipient admixture (1) at a temperature of less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. Moreover, in some embodiments a cool incipient admixture may be an admixture at about 5 degrees Celsius.

Now with further reference primarily to FIG. 2, some embodiments may include a compromised sorted sperm cell processing medium. The term processing medium may be understood to include any medium conducive to sperm cells in which sperm cells may be placed to undergo processing. Moreover, embodiments also may include a plurality of sperm cells selected for a desired characteristic, an unclarified protein-free sperm cell extender component, an unclarified protein-free cryoprotectant-containing sperm cell extender component, and an unclarified centrifugation medium (7) in which said plurality of sperm cells selected for a desired characteristic, said unclarified protein-free sperm cell extender component, and said unclarified protein-free cryoprotectant-containing sperm cell extender component are suspended. The term unclarified may be understood to include a substance maintained in an unclarified state, and the term unclarified state may be understood to include a state in which a substance may exist wherein such a substance has not been clarified. The term centrifugation medium may be understood to include any medium conducive to sperm cells that at some point is subjected to centrifugation.

Certain embodiments may further include an unclarified protein-containing sperm cell extender component suspended in an unclarified centrifugation medium (7). Moreover, such an unclarified centrifugation medium (7) in some embodiments may contain an egg yolk content. This may be a function, for example, of perhaps the amount of protein in such an unclarified protein-containing sperm cell extender component, perhaps wherein such protein may be egg yolk. In various embodiments, the percentage of egg yolk contained within an unclarified centrifugation medium (7) may include more than about 0.4 percent egg yolk, more than about 0.8 percent egg yolk, more than about 1.6 percent egg yolk, or perhaps even more than about 3.2 percent egg yolk. Some embodiments may include a percentage of egg yolk contained with an unclarified centrifugation medium (7) of about 1.6 percent. Moreover, in certain embodiments an unclarified centrifugation medium (7) may contain at least some glycerol and have less than about 11 percent egg yolk.

Moreover, in certain embodiments an unclarified centrifugation medium (7) may perhaps include a cool unclarified centrifugation medium (7). Such a cool unclarified centrifugation medium (7) perhaps may include an unclarified centrifugation medium (7) at a temperature of less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. In some embodiments, a cool unclarified centrifugation medium (7) may include an unclarified centrifugation medium (7) at a temperature of about 5 degrees Celsius.

In some embodiments, an unclarified centrifugation medium (7) may perhaps have a minimized number of localized high density regions (6), including perhaps even no localized high density regions (6). The term localized may be understood to include a region of an unclarified centrifugation medium (7) that may be concentrated within a small volume of such an unclarified centrifugation medium (7), including perhaps a volume of less than 3 percent, less that 2 percent, less 1 percent, less than 0.05 percent, or perhaps even less than 0.01 percent of the total volume of an unclarified centrifugation medium (7). The term localized high density region (6) may be understood to include localized regions of an unclarified centrifugation medium (7) having a substantially higher density than surrounding regions, including perhaps more than 10% of a surrounding density, more than 20% of a surrounding density, more than 30% of a surrounding density, more than 40% of a surrounding density, more than 50% of a surrounding density, more than 100% of a surrounding density, more than 200% of a surrounding density, more than 300% of a surrounding density, more than 400% of a surrounding density, or perhaps even more than 500% of a surrounding density.

Now with further reference primarily to FIG. 3, certain embodiments may include an intermediate compromised sorted sperm cell extension medium. A sperm cell extension medium may be understood to include any medium conducive to sperm cells in which sperm cells may be placed for extension. The term intermediate may be understood to include a sperm cell extension medium representing an intermediate step in a process of treating sperm cells. For example, in various embodiments such an intermediate step perhaps may include adding a cryoprotectant to a previously prepared sperm cell medium, adding protein content to a previously prepared sperm cell medium, or perhaps centrifuging a previously prepared sperm cell medium.

Moreover, further embodiments may include a plurality of sperm cells selected for a desired characteristic (8), a protein-free sperm cell extender component (9), a protein-free cryoprotectant-containing sperm cell extender component (10), and a protein-containing sperm cell extender component (11). Certain embodiments also may include a total protein content not exceeding about 1.6 percent (12). This may be a function, for example, of perhaps the amount of protein in a protein-containing sperm cell extender component of such an intermediate sperm cell extension medium. In some embodiments, the protein in a protein-containing sperm cell extender perhaps may be egg yolk. Accordingly, a total protein content not exceeding about 1.6 percent perhaps may include an egg yolk content not exceeding about 1.6 percent.

Certain embodiments may also include a cooled intermediate extension medium in which a plurality of sperm cells selected for a desired characteristic (8), protein-free sperm cell extender component (9), a protein-free cryoprotectant-containing sperm cell extender component (10), and a protein-containing sperm cell extender component (11) may be suspended. In some embodiments, such a cooled intermediate extension medium may include an intermediate extension medium at a temperature of perhaps less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, or perhaps even less than about 1 degree Celsius. In certain embodiments such a cooled intermediate extension medium may have a temperature of about 5 degrees Celsius.

Several advantages may attend the inventive technology. In particular, the use of a protein-free cryoprotectant-containing sperm cell extender in various embodiments may represent a significant improvement over previous sperm cell extenders. For example, the addition of such a protein-free cryoprotectant-containing sperm cell extender to other sperm cell extenders may reduce clumps or other locally dense regions due perhaps to lower concentrations of such proteins, perhaps including egg yolk. This may reduce or perhaps even eliminate the compaction of sperm cells in certain applications, for example centrifuging, that may cause damage to sperm cells. Additionally, the reduction of such clumps in a sperm cell extender may eliminate the need to clarify such an extender, resulting in related materials savings, labor savings, time savings, and financial savings. Further, a protein-free cryoprotectant-containing sperm cell extender may be less susceptible to the effects of spoliation. This may allow such a sperm cell extender to be prepared in large quantities ahead of time, rather than on an as-needed basis. Additionally, mitigating the effects of spoliation may reduce the risk of contamination by bacteria. Further, because such a sperm cell extender perhaps may be less sensitive to environmental conditions, it may be more able to be transported over large distances where environmental conditions may vary.

Accordingly, such a protein-free cryoprotectant-containing sperm cell extender may be an effective B fraction of a sperm cell extender in various applications. Moreover, it may be that use of such a protein-free cryoprotectant-containing sperm cell extender may not significantly adversely impact the effectiveness of a sperm cell extender in which it used. For example, in embodiments relating to artificial insemination techniques, the use of such a sperm cell extender perhaps may yield results that are not significantly different than those achieved with the use of typical sperm cell extenders. In particular, pregnancy rates achieved with such a sperm cell extender in various embodiments perhaps may be comparable to those achieved with typical sperm cell extenders, including perhaps even being statistically comparable (P>0.05) in various embodiments.

Several examples may be reported using the inventive technology as herein described. Importantly, these examples should be understood to represent only some embodiments of the inventive technology. Accordingly, it may be appreciated that these examples should not be construed as limiting the scope of the inventive technology herein described.

EXAMPLE 1

One possible procedure for collecting and processing sorted sperm involving a B-fraction of an extender containing egg yolk may be as follows. Tris-A catch medium (2-ml) may be deposited in a 50-ml Falcon tube. Sorted sperm may be collected into the 50-ml Falcon tube over the course of approximately 1 hour for a total sorted volume of 12.5-ml. This volume may be non-glycerol containing and may be referred to as the A-fraction. The percent of egg yolk in the A-fraction for this example is 3.2% [(2-ml "Catch")/(12.5-ml total volume)×(20% egg yolk "Catch")=3.2%)]. The 3.2% egg yolk admixture may be cooled to 5° C. over perhaps 90-min. Following the cooling period, an equal volume of glycerol-containing 20% egg yolk extender (B-fraction; 12% glycerol) may be added stepwise as 2 equal fractions at perhaps 15-min intervals. Cooled sorted sperm, now contained in this example in an 11.6% egg yolk ABextender [((12.5-ml A-fraction)×(3.2% egg yolk)+(12.5-ml B-fraction)×(20% egg yolk))/25-ml total volume=11.6% egg yolk] may be centrifuged for concentration. This method of adding the glycerol-containing extender to cooled sperm may avoid over extension of sperm pellets that may occur when non-sperm containing droplets are perhaps collected in the sorting process, if the sperm pellet is left in too much volume, and may assure that the final glycerol content is always 6%. A 200-μl sperm pellet may remain after removal of the supernatant. Sperm pellets from the same male may be pooled and total volume may be determined by weight. The number of total sorted sperm may be determined, perhaps with multiple hemacytometer counts, and the sperm concentration of the pellet may be adjusted to a desired freezing concentration, perhaps with 20% egg yolk AB extender.

In this example, if the sperm concentration in the 12.5-ml sorted volume is $1 \times 10^6$ sperm/ml, representing $12.5 \times 10^6$ total sperm, and the post-centrifuge recovery rate is 85%, then the sperm concentration in the 200-μ sperm pellet is $\sim 53 \times 10^6$ sperm/ml ($10.6 \times 10^6$ total sperm). If a freezing concentration of $10 \times 10^6$ sperm/ml is desired for this methodology, then 860-μl of 20% egg yolk AB extender may be added to the 200-μl sperm pellet. Based on this model, the final egg yolk percent for freezing sorted sperm is 18.4% [((0.200-ml sperm pellet)×(11.6% egg yolk)+(0.860-ml AB extender)×(20% egg yolk))/1.06-ml total volume=18.4% final egg yolk].

Using the above example, but substituting 0% egg yolk B-extender in place of 20% egg yolk B-extender, the percent of egg yolk contained in the 25-ml volume to be centrifuged is 1.6% [((12.5-ml A-fraction)×(3.2% egg yolk)+(12.5-ml B-fraction)×(0% egg yolk))/25-ml total volume=1.6% egg yolk]. If the sperm pellet in this example is adjusted to a final freezing concentration of $10 \times 10^6$ sperm/ml with 20% egg yolk AB extender, the final egg yolk percent is 16.5% [((0.200-ml sperm pellet)×(1.6% egg yolk)+(0.860-ml AB-extender)×(20% egg yolk))+1.06-ml total volume=16.5% egg yolk].

Accordingly, it may be seen that the final egg yolk percentage may perhaps vary only slightly between the two different B-fraction extenders. When using the 0% egg yolk B-extender, the final egg yolk percentage may be less when higher sperm concentrations (>$10 \times 10^6$ sperm/ml) are desired.

EXAMPLE 2

A further example may be reported as follows. Sperm were studied from first ejaculates obtained from 6 bulls and the study was replicated three times. Sperm for this study were not sorted but were subjected to Hoechst 33342 staining and extreme dilution as occurs during sorting. The objective was to compare post-thaw motility of sperm that received glycerol-containing extender (B-fraction) with or without egg yolk. An additional objective was to identify the optimal glycerol content needed for sorted sperm. Therefore, 3, 4, 5 and 6% final glycerol content was studied in both 0 and 20% egg yolk containing B-fraction extender. Sperm frozen in 0.25-ml straws were thawed in a 37° C. water bath for 30 sec and were incubated at 37° C. Visual estimates of total motility were determined by 2 observers, blind to treatment, at 30 and 120 min of incubation.

Figure 4:
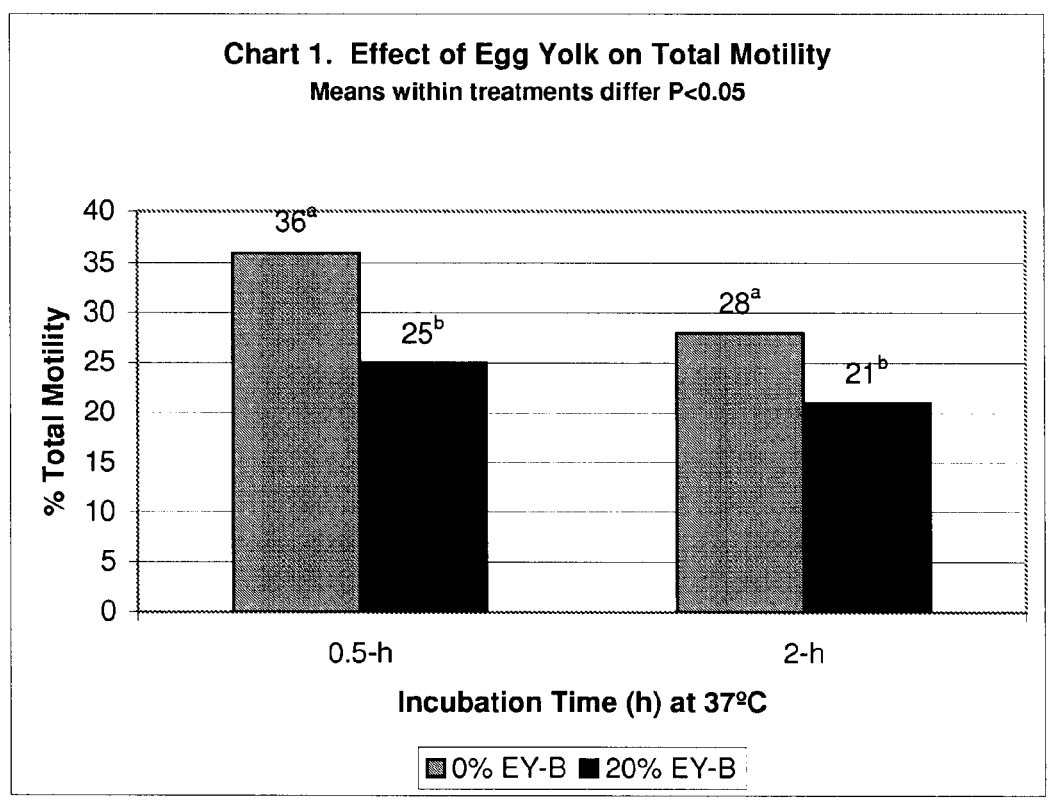
FIG. 4 is a chart showing the effect of egg yolk on total motility.

The exclusion of egg yolk in the B-fraction extender did not adversely affect post-thaw sperm motility. In fact, motility was statistically higher for sperm processed in B-fraction extender without egg yolk as compared to that with 20% egg yolk (P<0.05) at both incubation times. See FIG. 4.

A final glycerol concentration of 3% resulted in statistically lower motilities at 30-min and 120-min after thawing, while motilities were higher and did not differ as a function of 4-6% glycerol.

Figure 5:
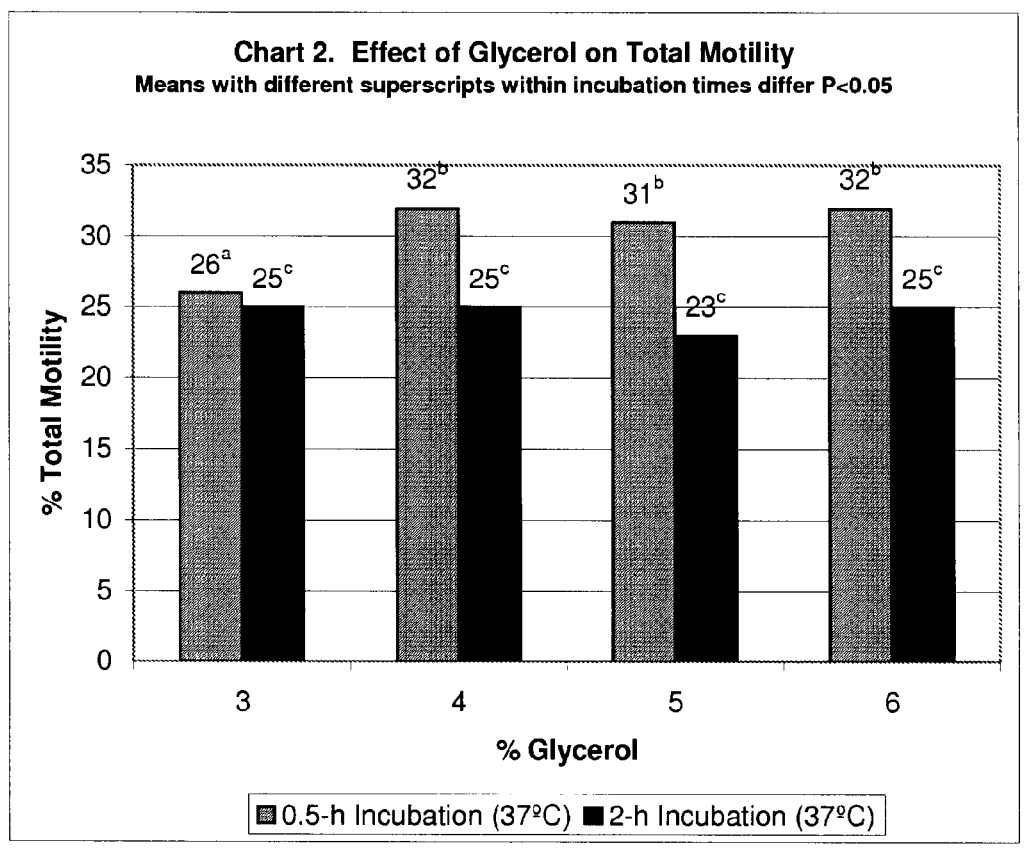
FIG. 5 is a chart showing the effect of glycerol on total motility.

See FIG. 5. From this example, it perhaps may be concluded that 3% glycerol did not provide adequate cryoprotection for sorted sperm. Since motilities did not differ between 4-6% glycerol, and the provision of adequate cryoprotection may be desirable (which may differ between bulls), a final concentration of 6% glycerol for sex sorted sperm cryopreservation may be appropriate.

EXAMPLE 3

Another example may be reported as follows. An objective was to compare 30-day pregnancy rate in Holstein heifers inseminated with X-chromosome bearing sperm that were processed with 0% egg yolk glycerol (12%) containing extender to that containing 20% egg yolk.

X-chromosome bearing sperm from each of 2 bulls were isolated on the basis of DNA content using a flow cytometer. Sorted sperm were collected in 50-ml plastic tubes containing 2-ml of 20% egg yolk-TRIS extender without glycerol until each tube contained 12.5-ml and approximately 12 million sperm. Sorted sperm were cooled (5° C.) over 90 minutes.

After cooling, sperm-containing sort tubes (50-ml Falcon) were evenly separated and glycerol-containing extender (B-fraction) added. Cooled sperm received either B-fraction extender containing 0% egg yolk or 20% egg yolk. Tubes containing sorted sperm (25-ml total volume) were then centrifuged at 850×g for 20-minutes at 5° C. Supernatant was removed, leaving sorted sperm in approximately 200-µl pellets. Like sperm pellets were pooled and adjusted to $10\times10^6$ sperm/ml with 20% egg yolk-AB medium (6% final glycerol content). Final egg yolk percentage in the product varied by sorting day (range: 16.5-18.2%). Sperm ($2\times10^6$) were packaged into 0.25-ml coded straws to ensure treatments were blind to AI technicians, placed on freezing racks and cryopreserved in $LN_2$ vapor. An equal number of straws from each bull and treatment were placed into goblets and attached to aluminum canes.

Sperm post-thaw motility was determined using "Track" motility after 30-min of incubation at 37° C. The mean percentage of progressively motile sperm for the freeze codes processed with 20% egg yolk B-fraction extender was 44% and that for the 0% egg yolk B-fraction extender was 43%.

119 non-synchronized Holstein heifers were balanced across the different egg yolk-media and 2 Holstein bulls. Insemination occurred 12 or 24 hours after observed standing estrus. Three inseminators were used in this example. Approximately 1 month after insemination, pregnancy was determined using ultrasound. Data were subjected to ANOVA.

Pregnancy rate did not differ (P>0.05) between sorted sperm processed with 0% egg yolk-"B" fraction extender to that for 20% egg yolk-"B" fraction extender. See Table 1.

Actual pregnancy rates were similar for bulls and AI technicians (P>0.05), and there were no statistical interactions. Numerically, the pregnancy rate for bull 52H0039 was higher than for bull 52H0038. See Table 2. A larger sampling of the population may have resulted in a significant difference in pregnancy rate between the two bulls. It may be important to note for this example that the 95% confident intervals (CI) are large.

TABLE 1

0% Egg Yolk vs. 20% Egg Yolk "B" Extender Field Trial by Treatment

| Treatment | (n) | Pregnant (%) ± S.E.M. | 95% CI |
|---|---|---|---|
| 0% Egg Yolk-"B" | 59 | 56 ± 0.065 | 43-68 |
| 20% Egg Yolk-"B" | 60 | 55 ± 0.065 | 42-67 |

Actual means are presented.
Bulls (n = 2), AI technicians (n = 3) and Treatments (n = 2) were similar (P > 0.05).

TABLE 2

0% Egg Yolk vs. 20% Egg Yolk "B" Extender Field Trial by Bull

| Bull # | (n) | Pregnant (%) ± S.E.M. | 95% CI |
|---|---|---|---|
| 52HO039 | 60 | 62 ± 0.063 | 49-73 |
| 52HO038 | 59 | 49 ± 0.065 | 38-62 |

Actual means are presented.
Bulls (n = 2) were similar (P > 0.05).

As may be easily understood from the foregoing, the basic concepts of the present invention may be embodied in a variety of ways. It involves both sperm cell extending techniques as well as devices to accomplish the appropriate sperm cell extension. In this application, the sperm cell extending techniques are disclosed as part of the results shown to be achieved by the various devices described and as steps that are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included herein is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element that causes that action. Similarly, each physical element disclosed should be understood to encompass a disclosure of the action that that physical element facilitates. Regarding this last aspect, as but one example, the disclosure of an "extender" should be understood to encompass disclosure of the act of "extending"—whether explicitly discussed or not—and, conversely, were there effectively disclosure of the act of "extending", such a disclosure should be understood to encompass disclosure of an "extender" and even a "means for extending" Such changes and alternative terms are to be understood to be explicitly included in the description.

Any patents, publications, or other references mentioned in this application for patent are hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the Information Disclosure Statement or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the sperm cell extender devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, and xii) each potentially dependent claim or concept as a dependency on each and every one of the independent claims or concepts presented.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The invention claimed is:

1. A method for freezing sorted sperm cells compromised by a sorting event comprising the steps of:
   obtaining a plurality of sperm cells;
   subjecting said plurality of sperm cells to sorting stresses;
   selecting said plurality of sperm cells for a desired characteristic;
   adding a protein-containing sperm cell extender to said plurality of selected sperm cells to form a first extended sperm cell mixture;
   cooling said first extended sperm cell mixture to create a first cooled extended sperm cell mixture;
   adding a protein-free cryoprotectant-containing sperm cell extender to said first cooled extended sperm cell mixture to form a second cooled extended sperm cell mixture;
   freezing said second cooled extended sperm cell mixture.

2. A method for freezing sorted sperm cells compromised by a sorting event as described in claim 1, wherein said step of obtaining a plurality of sperm cells comprises the step of obtaining a plurality of mammalian sperm cells.

3. A method for freezing sorted sperm cells compromised by a sorting event as described in claim 2, wherein said step of obtaining a plurality of mammalian sperm cells comprises the step of obtaining a plurality of mammalian sperm cells selected from the group consisting of bovine sperm cells, equine sperm cells, porcine sperm cells, ovine sperm cells, cervid sperm cells, canine sperm cells, and delphinidae sperm cells.

4. A method for freezing sorted sperm cells compromised by a sorting event as described in claim 1, wherein said step of selecting said plurality of sperm cells to sorting stresses comprises the step of separating said selected sperm cells having a desired characteristic.

5. A method for freezing sorted sperm cells compromised by a sorting event as described in claim 4, wherein said step of separating said selected sperm cells having a desired characteristic comprises the step of separating said selected sperm cells having a desired characteristic by flow cytometery.

6. A method for freezing sorted sperm cells compromised by a sorting event as described in claim 5, wherein said step of adjusting a sperm cell concentration of said second cooled extended sperm cell mixture to a pre-freeze sperm cell concentration comprises the step establishing a pre-freeze egg yolk content of said second extended sperm cell mixture of about 16.5 percent.

7. A method for freezing sorted sperm cells compromised by a sorting event as described in claim 1, wherein said step of selecting said plurality of sperm cells for a desired characteristic comprises the step of selecting said plurality of sperm cells for a sex characteristic.

8. A method for freezing sorted sperm cells compromised by a sorting event as described in claim 7, wherein said step of selecting said plurality of sperm cells for a sex characteristic comprises the step of selecting said plurality of sperm cells for a sex characteristic selected from the group consisting of a X-chromosome-bearing characteristic and a Y-chromosome-bearing characteristic.

9. A method for freezing sorted sperm cells compromised by a sorting event as described in claim 1, wherein said step of adding a protein-containing sperm cell extender to said plurality of selected sperm cells to form a first extended sperm cell mixture comprises the step of adding an animal-based protein-containing sperm cell extender to said plurality of selected sperm cells to form a first extended sperm cell mixture.

10. A method for freezing sorted sperm cells compromised by a sorting event as described in claim 9, wherein said step of adding an animal-based protein-containing sperm cell extender to said plurality of selected sperm cells to form a first extended sperm cell mixture comprises the step of adding a lipoprotein-containing sperm cell extender to said plurality of selected sperm cells to form a first extended sperm cell mixture.

11. A method for freezing sorted sperm cells compromised by a sorting event as described in claim 10, wherein said step of adding a lipoprotein-containing sperm cell extender to said plurality of selected sperm cells to form a first extended sperm cell mixture comprises the step of adding an egg-yolk-containing sperm cell extender to said plurality of selected sperm cells to form a first extended sperm cell mixture.

12. A method for freezing sorted sperm cells compromised by a sorting event as described in claim 11, wherein said step of adding an egg-yolk-containing sperm cell extender to said plurality of selected sperm cells to form a first extended sperm cell mixture comprises the step of adding an egg-yolk-containing sperm cell extender having a percentage of egg yolk selected from the group consisting of less than about 50 percent egg yolk, less than about 45 percent egg yolk, less than about 40 percent egg yolk, less than about 35 percent egg yolk, less than about 30 percent egg yolk, less than about 25 percent egg yolk, less than about 20 percent egg yolk, less than about 15 percent egg yolk, less than about 10 percent egg yolk, and less than 5 percent egg yolk.

13. A method for freezing sorted sperm cells compromised by a sorting event as described in claim 12, wherein said step of adding an egg-yolk-containing sperm cell extender to said plurality of selected sperm cells to form a first extended sperm cell mixture comprises the step of adding an egg-yolk-containing sperm cell extender having about 20 percent egg yolk.

14. A method for freezing sorted sperm cells compromised by a sorting event as described in claim 13, wherein said step of adding an egg-yolk-containing sperm cell extender to said plurality of selected sperm cells to form a first extended sperm cell mixture comprises the step of adding an egg-yolk-containing sperm cell extender to said plurality of selected sperm cells to form a first extended sperm cell mixture having a percentage of egg yolk selected from the group consisting of more than about 0.8 percent egg yolk, more than about 1.6 percent egg yolk, more than about 3.2 percent egg yolk, and more than about 6.4 percent egg yolk.

15. A method for freezing sorted sperm cells compromised by a sorting event as described in claim 11, wherein said step of adding an egg-yolk-containing sperm cell extender to said plurality of selected sperm cells to form a first extended sperm cell mixture comprises the step of adding an egg-yolk-containing sperm cell extender to said plurality of selected sperm cells to form a first extended sperm cell mixture having about 3.2 percent egg yolk.

16. A method for freezing sorted sperm cells compromised by a sorting event as described in claim 1, wherein said step of adding a protein-containing sperm cell extender to said plurality of selected sperm cells to form a first extended sperm cell mixture comprises the step of adding a protein-containing sperm cell extender selected from the group consisting of an egg yolk based extender, a milk based extender, a citrate extender, a tris-hydroxymethyl-aminomethane (Tris) extender, and a N-tris(hydroxymethyl)methyl-2-aminoethane-sulfonic acid plus Tris (TEST) extender.

17. A method for freezing sorted sperm cells compromised by a sorting event as described in claim 1, wherein said step of cooling said first extended sperm cell mixture to create a first cooled extended sperm cell mixture comprises the step of cooling said first extended sperm cell mixture to a temperature selected from the group consisting of less than about 10 degrees Celsius, less than about 9 degrees Celsius, less than about 8 degrees Celsius, less than about 7 degrees Celsius, less than about 6 degrees Celsius, less than about 5 degrees Celsius, less than about 4 degrees Celsius, less than about 3 degrees Celsius, less than about 2 degrees Celsius, and less than about 1 degree Celsius.

18. A method for freezing sorted sperm cells compromised by a sorting event as described in claim 1, wherein said step of cooling said first extended sperm cell mixture to create a first cooled extended sperm cell mixture comprises the step of cooling said first extended sperm cell mixture to a temperature of about 5 degrees Celsius.

19. A method for freezing sorted sperm cells compromised by a sorting event as described in claim 1, wherein said step of adding a protein-free cryoprotectant-containing sperm cell extender to said first cooled extended sperm cell mixture to form a second cooled extended sperm cell mixture comprises the step of adding a glycerol-containing sperm cell extender to said first cooled extended sperm cell mixture to form a second cooled extended sperm cell mixture.

20. A method for freezing sorted sperm cells compromised by a sorting event as described in claim 19, wherein said step of adding a glycerol-containing sperm cell extender to said first cooled extended sperm cell mixture to form a second cooled extended sperm cell mixture comprises the step of adding a glycerol-containing sperm cell extender having a percentage of glycerol selected from the group consisting of more than about 3 percent glycerol, more than about 6 percent glycerol, more than about 12 percent glycerol, and more than about 24 percent glycerol.

21. A method for freezing sorted sperm cells compromised by a sorting event as described in claim 19, wherein said step of adding a glycerol-containing sperm cell extender to said first cooled extended sperm cell mixture to form a second cooled extended sperm cell mixture comprises the step of adding a glycerol-containing sperm cell extender having about 6 percent glycerol.

22. A method for freezing sorted sperm cells compromised by a sorting event as described in claim 1, wherein said step of adding a protein-free cryoprotectant-containing sperm cell extender to said first cooled extended sperm cell mixture to form a second cooled extended sperm cell mixture comprises the step of adding a protein-free cryoprotectant-containing sperm cell extender having a volume equal to a volume of said first cooled extended sperm cell mixture.

23. A method for freezing sorted sperm cells compromised by a sorting event as described in claim 22, further comprising the step of adding said protein-free cryoprotectant-containing sperm cell extender having a volume equal to a volume of said first cooled extended sperm cell mixture in two steps.

24. A method for freezing sorted sperm cells compromised by a sorting event as described in claim 1, wherein said step of adding a protein-free cryoprotectant-containing sperm cell extender to said first cooled extended sperm cell mixture to form a second cooled extended sperm cell mixture comprises the step of adding a sterile cryoprotectant-containing sperm cell extender to said first cooled extended sperm cell mixture to form a second cooled extended sperm cell mixture.

25. A method for freezing sorted sperm cells compromised by a sorting event as described in claim 1, wherein said step of adding a protein-free cryoprotectant-containing sperm cell extender to said first cooled extended sperm cell mixture to form a second cooled extended sperm cell mixture comprises the step of adding a low density gradient cryoprotectant-containing sperm cell extender to said first cooled extended sperm cell mixture to form a second cooled extended sperm cell mixture.

26. A method for freezing sorted sperm cells compromised by a sorting event as described in claim 25, wherein said step of adding a low density gradient cryoprotectant-containing sperm cell extender to said first cooled extended sperm cell mixture to form a second cooled extended sperm cell mixture comprises the step of adding a substantially liquid cryoprotectant-containing sperm cell extender to said first cooled extended sperm cell mixture to form a second cooled extended sperm cell mixture.

27. A method for freezing sorted sperm cells compromised by a sorting event as described in claim 25, wherein said step of adding a low density gradient cryoprotectant-containing sperm cell extender to said first cooled extended sperm cell mixture to form a second cooled extended sperm cell mixture comprises the step of adding a centrifugation-efficient cryoprotectant-containing sperm cell extender.

28. A method for freezing sorted sperm cells compromised by a sorting event as described in claim 25, wherein said step of adding a low density gradient cryoprotectant-containing sperm cell extender to said first cooled extended sperm cell mixture to form a second cooled extended sperm cell mixture comprises the step of adding a substantially uniform density cryoprotectant-containing sperm cell extender to said first cooled extended sperm cell mixture to form a second cooled extended sperm cell mixture.

29. A method for freezing sorted sperm cells compromised by a sorting event as described in claim 25, wherein said step of adding a low density gradient cryoprotectant-containing sperm cell extender to said first cooled extended sperm cell mixture to form a second cooled extended sperm cell mixture comprises the step of adding a cryoprotectant-containing sperm cell extender with substantially no sperm cell compaction particles.

30. A method for freezing sorted sperm cells compromised by a sorting event as described in claim 25, wherein said step of adding a low density gradient cryoprotectant-containing sperm cell extender to said first cooled extended sperm cell mixture to form a second cooled extended sperm cell mixture comprises the step of adding a low viscosity cryoprotectant-containing sperm cell extender to said first cooled extended sperm cell mixture to form a second cooled extended sperm cell mixture.

31. A method for freezing sorted sperm cells compromised by a sorting event as described in claim 1, wherein said step of adding a protein-free cryoprotectant-containing sperm cell extender to said first cooled extended sperm cell mixture to form a second cooled extended sperm cell mixture comprises the step of adding a protein-free cryoprotectant-containing sperm cell extender to said first cooled extended sperm cell mixture to form a second cooled extended sperm cell mixture having a percentage of egg yolk selected from the group consisting of more than about 0.4 percent egg yolk, more than about 0.8 percent egg yolk, more than about 1.6 percent egg yolk, and more than about 3.2 percent egg yolk.

32. A method for freezing sorted sperm cells compromised by a sorting event as described in claim 1, wherein said step of adding a protein-free cryoprotectant-containing sperm cell extender to said first cooled extended sperm cell mixture to form a second cooled extended sperm cell mixture comprises the step of adding a protein-free cryoprotectant-containing sperm cell extender to said first cooled extended sperm cell mixture to form a second cooled extended sperm cell mixture having about 1.6 percent egg yolk.

33. A method for freezing sorted sperm cells compromised by a sorting event as described in claim 1, further comprising the step of maintaining said second cooled extended sperm cell mixture in an unclarified state.

34. A method for freezing sorted sperm cells compromised by a sorting event as described in claim 33, further comprising the step of subjecting said unclarified second cooled extended sperm cell mixture to centrifugation.

35. A method for freezing sorted sperm cells compromised by a sorting event as described in claim 34, further comprising the step of decanting a portion of said centrifuged unclarified second cooled extended sperm cell mixture.

36. A method for freezing sorted sperm cells compromised by a sorting event as described in claim 1, further comprising the step of adjusting a sperm cell concentration of said second cooled extended sperm cell mixture to a pre-freeze sperm cell concentration.

37. A method for freezing sorted sperm cells compromised by a sorting event as described in claim 36, wherein said step of adjusting a sperm cell concentration of said second cooled extended sperm cell mixture to a pre-freeze sperm cell concentration comprises the step of adding a protein-containing sperm cell extender to said second extended sperm cell mixture.

38. A method for freezing sorted sperm cells compromised by a sorting event as described in claim 37, wherein said step of adding a protein-containing sperm cell extender to said second extended sperm cell mixture comprises the step of adding an animal-based protein-containing sperm cell extender to said second extended sperm cell mixture.

39. A method for freezing sorted sperm cells compromised by a sorting event as described in claim 38, wherein said step of adding an animal-based protein-containing sperm cell extender to said second extended sperm cell mixture comprises the step of adding a lipoprotein-containing sperm cell extender to said second extended sperm cell mixture.

40. A method for freezing sorted sperm cells compromised by a sorting event as described in claim 39, wherein said step of adding a lipoprotein-containing sperm cell extender to said second extended sperm cell mixture comprises the step of adding an egg-yolk-containing sperm cell extender to said second extended sperm cell mixture.

41. A method for freezing sorted sperm cells compromised by a sorting event as described in claim 40, wherein said step of adding an egg-yolk-containing sperm cell extender to said second extended sperm cell mixture comprises the step of adding an egg-yolk-containing sperm cell extender having a percentage of egg yolk selected from the group consisting of less than about 50 percent egg yolk, less than about 45 percent egg yolk, less than about 40 percent egg yolk, less than about 35 percent egg yolk, less than about 30 percent egg yolk, less than about 25 percent egg yolk, less than about 20 percent egg yolk, less than about 15 percent egg yolk, less than about 10 percent egg yolk, and less than 5 percent egg yolk.

42. A method for freezing sorted sperm cells compromised by a sorting event as described in claim 40, wherein said step of adding an egg-yolk-containing sperm cell extender to said second extended sperm cell mixture comprises the step of adding an egg-yolk-containing sperm cell extender having about 20 percent egg yolk.

43. A method for freezing sorted sperm cells compromised by a sorting event as described in claim 37, wherein said step of adding a protein-containing sperm cell extender to said second extended sperm cell mixture comprises the step of adding a protein-containing sperm cell extender having a percentage of glycerol selected from the group consisting of more than about 3 percent glycerol, more than about 6 percent glycerol, more than about 12 percent glycerol, and more than about 24 percent glycerol.

44. A method for freezing sorted sperm cells compromised by a sorting event as described in claim 37, wherein said step of adding a protein-containing sperm cell extender to said second extended sperm cell mixture comprises the step of adding a protein-containing sperm cell extender to said second extended sperm cell mixture having about 6 percent glycerol.

45. A method for freezing sorted sperm cells compromised by a sorting event as described in claim 36, wherein said step of adjusting a sperm cell concentration of said second cooled extended sperm cell mixture to a pre-freeze sperm cell concentration comprises the step of adjusting a sperm cell concentration of said second cooled extended sperm cell mixture to a species-appropriate pre-freeze sperm cell concentration.

46. A method for freezing sorted sperm cells compromised by a sorting event as described in claim 45, wherein said step of adjusting a sperm cell concentration of said second cooled extended sperm cell mixture to a species-appropriate pre-freeze sperm cell concentration comprises the step of adjusting a sperm cell concentration of said second cooled extended sperm cell mixture to a pre-freeze sperm cell concentration selected from the group consisting of a bovine pre-freeze sperm cell concentration, an equine pre-freeze sperm cell concentration, and a porcine pre-freeze sperm cell concentration, an ovine pre-freeze sperm cell concentration, a cervid pre-freeze sperm cell concentration, a canine pre-freeze sperm cell concentration, and a delphinidae pre-freeze sperm cell concentration.

47. A method for freezing sorted sperm cells compromised by a sorting event as described in claim 45, wherein said step of adjusting a sperm cell concentration of said second cooled extended sperm cell mixture to a species-appropriate pre-freeze sperm cell concentration comprises the step of adjusting a sperm cell concentration of said second cooled extended sperm cell mixture to a sperm cell concentration selected from the group consisting of less than about 100 million sperm cells per milliliter, less than about 50 million sperm cells per milliliter, less than about 40 million sperm cells per milliliter, less than about 30 million sperm cells per milliliter, less than about 20 million sperm cells per milliliter, less than about 15 million sperm cells per milliliter, less than about 10 million sperm cells per milliliter, less than about 5 million sperm cells per milliliter, and less than about 2 million sperm cells per milliliter.

48. A method for freezing sorted sperm cells compromised by a sorting event as described in claim 45, wherein said step of adjusting a sperm cell concentration of said second cooled extended sperm cell mixture to a species-appropriate pre-freeze sperm cell concentration comprises the step of adjusting a sperm cell concentration of said second cooled extended sperm cell mixture to about 10 million sperm cells per milliliter.

49. A method for freezing sorted sperm cells compromised by a sorting event as described in claim 36, wherein said step of adjusting a sperm cell concentration of said second cooled extended sperm cell mixture to a pre-freeze sperm cell concentration comprises the step of establishing a pre-freeze egg yolk content of said second extended sperm cell mixture selected from the group consisting of within about 50 percent of the pre-freeze egg yolk content of a typical method for freezing sorted sperm cells, within about 25 percent of the pre-freeze egg yolk content of a typical method for freezing sorted sperm cells, within about 20 percent of the pre-freeze egg yolk content of a typical method for freezing sorted sperm cells, within about 15 percent of the pre-freeze egg yolk content of a typical method for freezing sorted sperm cells, within about 10 percent of the pre-freeze egg yolk content of a typical method for freezing sorted sperm cells, within about 5 percent of the pre-freeze egg yolk content of a typical method for freezing sorted sperm cells, and within about 1 percent of the pre-freeze egg yolk content of a typical method for freezing sorted sperm cells.

50. A method for freezing sorted sperm cells compromised by a sorting event as described in claim 36, wherein said step of adjusting a sperm cell concentration of said second cooled extended sperm cell mixture to a pre-freeze sperm cell concentration comprises the step establishing a pre-freeze egg yolk content of said second extended sperm cell mixture selected from the group consisting of less than about 50 percent egg yolk, less than about 45 percent egg yolk, less than about 40 percent egg yolk, less than about 35 percent egg yolk, less than about 30 percent egg yolk, less than about 25 percent egg yolk, less than about 20 percent egg yolk, less than about 15 percent egg yolk, and less than about 10 percent egg yolk.

* * * * *